US 8,273,045 B2
Sep. 25, 2012

(12) United States Patent
Ceriani

(10) Patent No.: US 8,273,045 B2
(45) Date of Patent: Sep. 25, 2012

(54) METHOD FOR FITTING AN ORTHOPEDIC BRACE TO THE BODY

(75) Inventor: Dylann D. Ceriani, San Diego, CA (US)

(73) Assignee: Breg, Inc., Carlsbad, CA (US)

( * ) Notice: Subject to any disclaimer, the term of this patent is extended or adjusted under 35 U.S.C. 154(b) by 1314 days.

(21) Appl. No.: 11/067,305

(22) Filed: Feb. 25, 2005

(65) Prior Publication Data

US 2006/0155232 A1 Jul. 13, 2006

Related U.S. Application Data

(63) Continuation-in-part of application No. 11/039,056, filed on Jan. 12, 2005.

(51) Int. Cl.
*A61F 5/37* (2006.01)
*A61F 13/00* (2006.01)
*A61F 5/00* (2006.01)
*A61F 13/06* (2006.01)
*A61B 19/00* (2006.01)

(52) U.S. Cl. .............. 602/26; 602/5; 602/12; 602/16; 602/20; 602/23; 602/60; 602/61; 602/62; 128/846; 128/869; 128/878; 128/881; 128/882

(58) Field of Classification Search ............... 602/5, 16, 602/23, 26, 32–40, 12, 20, 13, 60–62; 128/846, 128/869, 878, 881–882; 5/882, 610, 616, 5/621–622, 624; 24/170, 515, 498; 606/237, 606/240–242, 345; 297/217.1, 217.3, 284.1, 297/284.4, 284.8, 354.1, 353

See application file for complete search history.

(56) References Cited

U.S. PATENT DOCUMENTS

| 401,933 A | 4/1889 | De Camp | |
|---|---|---|---|
| 552,143 A | 12/1895 | Rankin | |
| 649,237 A | 5/1900 | Dyson | |
| 3,439,672 A | 4/1969 | Fisher | 128/88 |
| 3,805,773 A | 4/1974 | Sichau | 128/80 E |
| 4,481,941 A | 11/1984 | Rolfes | 128/87 R |
| 4,489,718 A | 12/1984 | Martin | 128/80 C |
| 4,531,515 A | 7/1985 | Rolfes | 128/87 R |
| 4,620,532 A | 11/1986 | Houswerth | 128/80 C |
| 4,655,201 A | 4/1987 | Pirmantgen | 128/80 C |
| 4,776,326 A | 10/1988 | Young et al. | 128/80 F |
| 4,817,588 A | 4/1989 | Bledsoe | 128/80 C |
| 4,982,732 A * | 1/1991 | Morris | 602/16 |
| 5,000,169 A | 3/1991 | Swicegood et al. | 128/80 C |
| 5,018,514 A | 5/1991 | Grood et al. | 128/80 C |
| 5,052,379 A | 10/1991 | Airy et al. | 128/80 C |
| 5,062,858 A | 11/1991 | Broeck et al. | 623/43 |
| 5,138,911 A | 8/1992 | Lan | 81/177.2 |
| 5,292,303 A | 3/1994 | Bastyr et al. | 602/16 |
| 5,409,449 A | 4/1995 | Nebolon | 602/16 |
| 5,443,444 A | 8/1995 | Pruyssers | 602/26 |
| 5,460,599 A | 10/1995 | Davis et al. | 602/26 |

(Continued)

*Primary Examiner* — Patricia Bianco
*Assistant Examiner* — Brandon L Jackson
(74) *Attorney, Agent, or Firm* — Rodney F. Brown

(57) ABSTRACT

A method is provided for securely fitting an orthopedic brace to the body by means of a plurality of straps, strap locks, strap attachment members, and strap connection members. The method retains the close fit of the brace to the body without the need for substantial readjustment of the fit even after repeated removal and remounting of the brace on the body. The method also enables repositioning the brace on the body without requiring removal of the brace from the body or substantial readjustment of the fit.

19 Claims, 11 Drawing Sheets

U.S. PATENT DOCUMENTS

| | | | |
|---|---|---|---|
| 5,621,953 A * | 4/1997 | Fildan | 24/170 |
| 5,653,680 A | 8/1997 | Cruz | 602/21 |
| 5,658,241 A | 8/1997 | Deharde et al. | 602/5 |
| 5,658,243 A | 8/1997 | Miller et al. | 602/26 |
| 5,672,152 A | 9/1997 | Mason et al. | 602/26 |
| 5,814,000 A | 9/1998 | Kilbey | 602/16 |
| 5,817,040 A | 10/1998 | Hess et al. | 602/26 |
| 5,827,208 A | 10/1998 | Mason et al. | 602/16 |
| 5,921,946 A | 7/1999 | Tillinghast et al. | 602/16 |
| 6,383,156 B1 * | 5/2002 | Enzerink et al. | 602/16 |
| 6,553,572 B2 * | 4/2003 | Fiorini et al. | 2/22 |
| 6,669,659 B2 * | 12/2003 | Dittmer et al. | 602/5 |
| 6,912,729 B2 * | 7/2005 | Nishimoto | 2/22 |
| 6,926,685 B1 * | 8/2005 | Modglin | 602/5 |
| 7,097,627 B2 * | 8/2006 | Enzerink et al. | 602/23 |
| 7,128,723 B2 * | 10/2006 | Doty et al. | 602/16 |
| 2001/0022013 A1 * | 9/2001 | Hsieh | 24/170 |
| 2001/0039696 A1 * | 11/2001 | Maciejczyk | 24/170 |
| 2002/0072695 A1 | 6/2002 | Doty et al. | 602/5 |
| 2002/0183672 A1 | 12/2002 | Enzerink et al. | 602/16 |
| 2003/0019080 A1 * | 1/2003 | Anthony et al. | 24/68 R |
| 2003/0172499 A1 * | 9/2003 | Uehara et al. | 24/170 |
| 2004/0031129 A1 * | 2/2004 | Yang | 24/170 |
| 2005/0070831 A1 * | 3/2005 | Cormier et al. | 602/26 |
| 2005/0192523 A1 * | 9/2005 | Knecht et al. | 602/26 |

* cited by examiner

METHOD FOR FITTING AN ORTHOPEDIC BRACE TO THE BODY

This is a continuation in part application of Ser. No. 11/039,056 filed on Jan. 12, 2005, which is incorporated herein by reference.

TECHNICAL FIELD

The present invention relates generally to orthopedic braces, and more particularly to a method for securely fitting an orthopedic brace to the body.

BACKGROUND OF THE INVENTION

Orthopedic braces are worn on the body of a user either to support a healthy skeletal joint that is at risk of injury or to stabilize a skeletal joint that has been destabilized by an injury or other condition. Orthopedic braces generally include rigid structural components to support or stabilize the skeletal joint. Frequently, although not necessarily, the rigid structural components are dynamically linked together by one or more hinges enabling controlled pivotal movement of the skeletal joint during user activity or rehabilitative therapy. The orthopedic brace is mounted on the body such that the hinges traverse the skeletal joint, while the rigid components are secured to the body above and below the skeletal joint by one or more straps. It is desirable to closely fit the orthopedic brace to the body on which the brace is mounted so that the orthopedic brace is maintained in a fixed position relative to the body even during periods of physical activity.

A close fit is typically enabled by tightening the straps of the orthopedic brace around the body to shorten the length of the straps. The shortened length of the straps is then set to maintain the fit of the orthopedic brace on the body thereafter. However, it is frequently desirable to remove the orthopedic brace from the body after a period of wearing the orthopedic brace. For example, removal of the brace may be desirable when the user anticipates a period of relative inactivity. The user remounts the orthopedic brace on the body when a period of physical activity is contemplated again.

Removal of the orthopedic brace from the body frequently requires the user to loosen the straps by lengthening them. Thus, it is necessary to refit the orthopedic brace to the body by readjusting the length of the straps when the user remounts the orthopedic brace on the body. Readjustment of the fit of an orthopedic brace to the body every time the orthopedic brace is removed and subsequently remounted on the body can be time-consuming and tedious. In addition, the probability of the user achieving a repeatable close fit with each readjustment diminishes with each removal and remounting sequence. Accordingly, it is an object of the present invention to provide an improved method for fitting an orthopedic brace to the body of a user. In particular, it is an object of the present invention to provide a method for closely fitting an orthopedic brace to the body of a user, wherein the close fit is readily repeatable after removing the orthopedic brace from the body and remounting the orthopedic brace on the body any number of times. It is another object of the present invention to provide a method for closely fitting an orthopedic brace to the body of a user, wherein the orthopedic brace can be repositioned relative to the body without removing the orthopedic brace from the body or altering the fit of the orthopedic brace to the body. These objects and others are accomplished in accordance with the invention described hereafter.

SUMMARY OF THE INVENTION

The present invention is characterized as a method for fitting an orthopedic brace to a body section of a user and subsequently readjusting the position of the orthopedic brace on the body section of the user. The method includes providing an orthopedic brace including a first longitudinal brace assembly, a second longitudinal brace assembly, a first strap, and a second strap. Each of the first and second straps has a first end and a second end and is segmented into a first side segment on a first side of the orthopedic brace and a second side segment on a second side of the orthopedic brace. The first side segments connect the first and second longitudinal brace assemblies to one another on the first side of the orthopedic brace. A body section is positioned between the first and second longitudinal brace assemblies and the second side segments connect the first and second longitudinal brace assemblies to one another about the body section on the second side of the orthopedic brace.

The first and second straps are releasably fixably connected to the first longitudinal brace assembly, thereby fixing the first and second side segments to desired fixed lengths corresponding to one or more dimensions of the body section. Fixable connection of the first and second straps to the first longitudinal brace assembly is released thereafter and the first longitudinal brace assembly or the second longitudinal brace assembly is repositioned relative to the body section. The first and second straps are then fixably reconnected to the first longitudinal brace assembly.

In accordance with a specific embodiment of the present characterization, the orthopedic brace is a knee brace and the body section is a leg having a lateral side and a medial side and having an upper leg, a lower leg and a knee joint. The first longitudinal brace assembly is a lateral longitudinal brace assembly including a lateral upper support arm positioned adjacent the upper leg on the lateral side, a lateral central joint positioned adjacent the knee joint, and a lateral lower support arm positioned adjacent the lower leg on the lateral side after positioning the body section between the lateral and medial longitudinal brace assemblies. The second longitudinal brace assembly is a medial longitudinal brace assembly including a medial upper support arm positioned adjacent the upper leg on the medial side, a medial central joint positioned adjacent the knee joint on the medial side, and a medial lower support arm positioned adjacent the lower leg on the medial side likewise after positioning the body section between the lateral and medial longitudinal brace assemblies.

The first side segment is preferably a posterior segment and the second side segment is preferably an anterior segment. The first strap is preferably an upper strap connecting the lateral and medial longitudinal brace assemblies to one another above the knee joint and the second strap is preferably a lower strap connecting the lateral and medial longitudinal brace assemblies to one another below the knee joint.

In accordance with another specific embodiment of the present characterization, the first and second longitudinal brace assemblies each has a first support arm, a second support arm, a central joint rotatably joining the first and second support arms, a first housing telescopingly displaceable relative to the central joint along the first support arm and a second housing telescopingly displaceable relative to the central joint along the second support arm. The method further comprises displacing the first housing relative to the central joint and/or displacing the second housing relative to the central joint after positioning the body section between the first and second longitudinal brace assemblies.

Another characterization of the present invention is a method for fitting a knee brace to a leg of a user and subsequently repositioning the orthopedic brace on the leg of the user. The method includes providing a knee brace including a first essentially rigid support member, a second essentially rigid support member, and a strap. The first support member is positioned on a first side of a leg above or below a knee joint and the second support member is positioned on a second side of the leg above or below the knee joint. The strap engages the first and second support members and the leg is encircled with an encircling segment of the strap. The encircling segment of the strap is tightened about the leg and the strap is fixably connected to the first and second support members, thereby fixing the encircling segment at a desired fixed length in correspondence with one or more dimensions of the leg to retain the first and second support members in position on the leg.

The strap is disconnected from the first support member while maintaining engagement with the first support member and maintaining the desired fixed length of the encircling segment. The first support member is repositioned on the first side of the leg or the second support member is repositioned on the second side of the leg while maintaining the desired fixed length of the encircling segment. The strap is then fixably reconnected to the first support member.

In accordance with a specific embodiment of the present characterization, the support member is a first support arm attached to a first rotatable hinge and the second support member is a second support arm attached to a second rotatable hinge. The first side of the leg is a lateral side and the second side of the leg is a medial side.

Another characterization of the present invention is a method for fitting an orthopedic brace to a body section of a user. The method includes providing an orthopedic brace having a first longitudinal brace assembly, a second longitudinal brace assembly, a first strap, a second strap, a third strap, a fourth strap, a first strap attachment member, a second strap attachment member, a third strap attachment member, and a fourth strap attachment member. Each of the first, second, third and fourth straps has a first end and a second end and is segmented into a first side segment on a first side of the orthopedic brace, a second side segment on a second side of the orthopedic brace, and a second end segment. The first longitudinal brace assembly has a first strap guide member, a second strap guide member, a third strap guide member and a fourth strap guide member. Each of the first, second, third and fourth strap guide members has a strap lock mounted thereon. The second longitudinal brace assembly has a first strap connection member, a second strap connection member, a third strap connection member and a fourth strap connection member.

The first side segment of each of the first, second, third and fourth straps is slidably engaged with each of the first, second, third and fourth strap guide members, respectively, and each of the first side segments is fixably attached to each of the first, second, third and fourth strap connection members, respectively, to set an arbitrary length of each of the first side segments and to connect the first and second longitudinal brace assemblies to one another by means of the first side segments.

The second side segment of each of the first, second, third and fourth straps is slidably engaged with each of the first, second, third and fourth strap guide members, respectively. Each of the second side segments is attached to each of the first, second, third and fourth strap attachment members to set an arbitrary length of each of the second side segments, while maintaining each of the second side segments disconnected from each of the first, second, third and fourth strap connection members, respectively. The strap lock of each of the first, second, third and fourth strap guide members is maintained in an open position so that each of the strap locks is disengaged from each of the first, second, third and fourth straps, respectively.

A body section is positioned between the first and second longitudinal brace assemblies. Each of the first, second, third and fourth strap attachment members is coupled with each of the first, second, third and fourth strap connection members, respectively, so that the second side segments connect the first and second longitudinal brace assemblies to one another about the body section. The second side segments is displaced to slide each of the first, second, third and fourth straps through each of the first, second, third and fourth strap guide members, respectively, to render the first side segments more taut. Each of the strap locks is transitioned from the open position to a closed position, thereby changing each of the first side segments from the arbitrary length to a desired fixed length. The second end segments are displaced to slide each of the first, second, third and fourth straps through each of the first, second, third and fourth strap attachment members, respectively, to render the second side segments more taut and change the second side segments from the arbitrary length to a desired fixed length.

In accordance with a specific embodiment of the present characterization, the method further comprises uncoupling each of the first, second, third and fourth strap attachment members from each of the first, second, third and fourth strap connection members, respectively, so that the first and second longitudinal brace assemblies are disconnected from one another on the second side of the orthopedic brace. The first and second longitudinal brace assemblies are removed from about the body section while maintaining the first side segments and second side segments at the desired fixed lengths. The specific embodiment still further comprises repositioning the body section between the first and second longitudinal brace assemblies and recoupling each of the first, second, third and fourth strap attachment members with each of the first, second, third and fourth strap connection members, respectively, so that the second side segments connect the first and second longitudinal brace assemblies to one another, while maintaining the first side segments and second side segments at the desired fixed lengths during the repositioning and recoupling steps.

In accordance with another specific embodiment of the present characterization, the body section is a leg having a lateral side and a medial side and having an upper leg, a lower leg and a knee joint, further wherein the orthopedic brace is a knee brace, the first longitudinal brace assembly is a lateral longitudinal brace assembly including a lateral upper support arm positioned adjacent the upper leg on the lateral side, a lateral central joint positioned adjacent the knee joint, and a lateral lower support arm positioned adjacent the lower leg on the lateral side and the second longitudinal brace assembly is a medial longitudinal brace assembly including a medial upper support arm positioned adjacent the upper leg on the medial side, a medial central joint positioned adjacent the knee joint on the medial side, and a medial lower support arm positioned adjacent the lower leg on the medial side after positioning the body section between the lateral and medial longitudinal brace assemblies.

The first side segment is a posterior segment and the second side segment is an anterior segment. The first strap is an upper distal strap, the second strap is an upper proximal strap, the third strap is a lower proximal strap, and the fourth strap is a lower distal strap. The first strap attachment member is an upper distal strap attachment member, the second strap attachment member is an upper proximal strap attachment member, the third strap attachment member is a lower proximal strap attachment member, and the fourth strap attachment member is a lower distal strap attachment member. The first strap guide member is an upper distal strap guide member, the second strap guide member is an upper proximal strap guide member, the third strap guide member is a lower proximal strap guide member, the fourth strap guide member is a lower distal strap guide member. The first strap connection member is an upper distal strap connection member, the second strap connection member is an upper proximal strap connection member, the third strap connection member is a lower proximal strap connection member and the fourth strap connection member is a lower distal strap connection member.

In accordance with a still another specific embodiment of the present characterization, the first and second longitudinal brace assemblies each has a first support arm, a second support arm, a central joint rotatably joining the first and second support arms, a first housing telescopingly displaceable relative to the central joint along the first support arm and a second housing telescopingly displaceable relative to the central joint along the second support arm. The method further comprises displacing the first housing relative to the central joint and/or displacing the second housing relative to the central joint after positioning the body section between the first and second longitudinal brace assemblies. Alternatively, the method further comprises displacing the first housing relative to the central joint and/or displacing the second housing relative to the central joint after coupling the second and third strap attachment members with the second and third strap connection members, respectively, but before coupling the first and fourth strap attachment members with the first and fourth strap connection members, respectively.

In accordance with yet another specific embodiment of the present characterization, the method further comprises transitioning the strap locks from the closed position to the open position, readjusting the positioning of the body section relative to the first longitudinal brace assembly or the second longitudinal brace assembly, and transitioning the strap locks from the open position to the closed position.

The present invention will be further understood from the drawings and the following detailed description.

DESCRIPTION OF PREFERRED EMBODIMENTS

Figure 1:
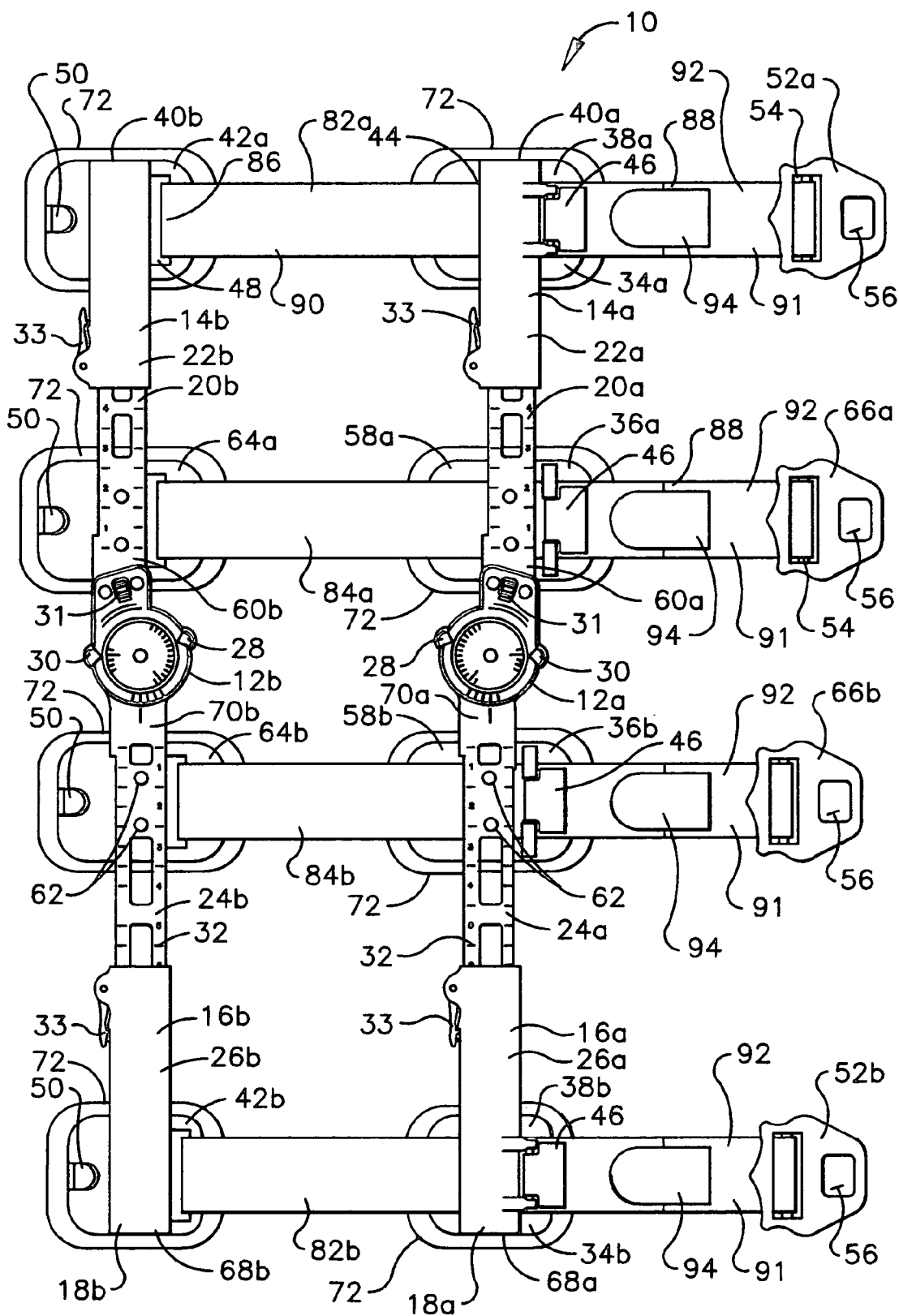
FIG. 1 is a plan view of an orthopedic brace mountable on the leg of a user in accordance with the fitting method of the present invention.

Referring initially to FIG. 1, an orthopedic brace is shown and generally designated 10, which has utility in a method of the present invention. There are a number of relative terms defined below which are used in the following description to distinguish various elements of the orthopedic brace 10 from one another, but which are not to be construed as limiting the scope of the invention. The relative terms "medial" and "lateral" characterize certain elements of the orthopedic brace 10 and, in particular, describe the relative proximity of the given element to the central longitudinal axis of the body of the user when the brace 10 is mounted thereon. A "medial" element is closer to the central longitudinal axis of the body, while a "lateral" element is further from the central longitudinal axis of the body.

The terms "proximal" and "distal" characterize certain elements of the brace 10, which are aligned with the longitudinal axis of the brace 10. The terms describe the relative proximity of the given element to the central joint of the brace 10. A "proximal" element is closer to the central joint of the brace 10, while a "distal" element is further from the central joint of the brace 10. The terms "upper" and "lower" likewise characterize certain elements of the brace 10, which are aligned with the longitudinal axis of the brace 10. However, the terms describe the position of the given element as being either above or below a horizontal plane running through the central joint of the brace 10. In particular, an "upper" element is above the horizontal plane running through the central joint of the brace 10, while a "lower" element is below the horizontal plane running through the central joint of the brace 10.

The relative terms "posterior" and "anterior" characterize certain elements of the orthopedic brace 10 and, in particular, describe the orientation of the given element relative to the central longitudinal axis of the body of the user when the brace 10 is mounted thereon. A "posterior" element is positioned behind the central longitudinal axis of the body in correspondence with the posterior of the body, while an "anterior" element is positioned in front of the central longitudinal axis of the body in correspondence with the posterior of the body.

The orthopedic brace 10 comprises a lateral central joint 12a, a lateral upper support assembly 14a and a lateral lower support assembly 16a, which in combination define a lateral longitudinal brace assembly 18a. The lateral upper support assembly 14a includes a lateral upper support arm 20a and a lateral upper housing 22a. The lateral lower support assembly 16a similarly includes a lateral lower support arm 24a and a lateral lower housing 26a, having a construction essentially similar to the lateral upper support arm 20a and lateral upper housing 22a, respectively. The lateral central joint 12a connects the lateral upper support assembly 14a with the lower support assembly 16a such that the lateral upper and lower support assemblies 14a, 16a extend radially from the lateral central joint 12a. Details of the lateral upper and lower support assemblies 14a, 16a are described below in association with the length-adjusting and locking mechanisms of the present invention.

The lateral central joint 12a is preferably a dynamic joint, which dynamically connects the lateral upper and lower support assemblies 14a, 16a, and is more preferably a rotational hinge, which rotationally connects the lateral upper and lower support assemblies 14a, 16a. The lateral central joint 12a is most preferably a releasably locking rotational hinge with adjustable rotation limits as shown herein. The releasably locking rotational hinge includes a flexion rotation stop 28, an extension rotation stop 30 and a lock actuator 31. Further details of the structure and operation of the releasably locking rotational hinge are disclosed in a commonly-owned copending patent application Ser. No. 11/039,448 filed on Jan. 12, 2005, which is incorporated herein by reference.

Notwithstanding the above, it is understood that the lateral central joint 12a is not limited to any one specific construction or type of joint. Thus, most conventional hinges for orthopedic braces, which enable rotation of the lateral upper longitudinal support assembly 14a and/or the lateral lower longitudinal support assembly 16a about the hinge, are alternatively employed as the lateral central joint 12a of the orthopedic brace 10. Exemplary prior art hinges are disclosed in U.S. Pat. Nos. 401,933; 4,481,941; 5,672,152; and 5,827,208. In yet another alternative, not shown, the lateral central joint 12a is a static joint which does not enable rotation of the lateral upper longitudinal support assembly 14a and/or the lateral lower longitudinal support assembly 16a about the joint. In accordance with this embodiment, the positions of the lateral upper support assembly 14a, lateral lower support assembly 16a, and lateral central joint 12a are all fixed relative to one another and the resulting orthopedic brace 10 functions solely as a splint.

The lateral upper support arm 20a is telescopingly fitted within the lateral upper housing 22a and the lateral lower support arm 24a is telescopingly fitted within the lateral lower housing 26a such that the lateral upper and lower housings 22a, 26a are slidably displaceable relative to the lateral central joint 12a along the length of the lateral upper and lower support arms 20a, 24a, respectively. This construction provides a length-adjusting mechanism which enables the practitioner to adjust the length of the lateral upper and lower support assemblies 14a, 16a in correspondence with the dimensions of a user on which the orthopedic brace 10 is to be mounted. The lateral upper and lower support arms 20a, 24a are each provided with a plurality of graduated length markers 32, which enable the user to determine the selected length of the lateral upper and lower support assemblies 14a, 16a. The lateral upper and lower housings 22a, 26a are further each provided with a locking mechanism which includes a lock lever 33. The lock levers 33 are selectively transitionable between a closed or locked position shown in FIG. 1 and an open or unlocked position. When the lock levers 33 are in the closed position, the locking mechanisms essentially prevent slidable displacement of the lateral upper and lower housings 22a, 26a along the length of the lateral upper and lower support arms 20a, 24a, respectively. When the lock levers 33 are in the open position, the locking mechanisms do not inhibit the user from slidably displacing the lateral upper and lower housings 22a, 26a.

The orthopedic brace 10 further comprises a medial central joint 12b, a medial upper support assembly 14b and a medial lower support assembly 16b, which in combination define a medial longitudinal brace assembly 18b. The construction of the medial longitudinal brace assembly 18b is essentially the same as the lateral longitudinal brace assembly 18a. As such, the medial upper support assembly 14b includes a medial upper support arm 20b and a medial upper housing 22b and the medial lower support assembly 16b similarly includes a medial lower support arm 24b and a medial lower housing 26b. The medial central joint 12b connects the medial upper support assembly 14b with the medial lower support assembly 16b such that the medial upper and lower support assemblies 14b, 16b extend radially from the medial central joint 12b.

The medial upper support arm 20b is telescopingly fitted within the medial upper housing 22b and the medial lower support arm 24b is telescopingly fitted within the medial lower housing 26b such that the medial upper and lower housings 22b, 26b are slidably displaceable relative to the medial central joint 12b along the length of the medial upper and lower support arms 20b, 24b, respectively. This construction provides a length-adjusting mechanism which enables the practitioner to adjust the length of the medial upper and lower support assemblies 14b, 16b in the same manner as the lateral upper and lower support assemblies 14a, 16a. The medial upper and lower support arms 20b, 24b are similarly each provided with the graduated length markers 32, which enable the user to determine the selected length of the medial upper and lower support assemblies 14b, 16b. The medial upper and lower housings 22b, 26b are further each provided with the locking mechanism having the lock lever 33 selectively transitionable between the closed or locked position and the open or unlocked position. When the lock levers 33 are in the closed position, the locking mechanisms essentially prevent slidable displacement of the medial upper and lower housings 22a, 26a. When the lock levers 33 are in the open position, the locking mechanisms do not inhibit the user from slidably displacing the medial upper and lower housings 22a, 26a.

The orthopedic brace 10 additionally comprises an upper distal strap retention assembly 34a and an upper proximal strap retention assembly 36a, both of which are associated with the lateral and medial upper support assemblies 14a, 14b. The upper distal strap retention assembly 34a includes an upper distal strap guide member 38a integral with a distal end 40a of the lateral upper housing 22a and an upper distal strap connection member 42a integral with a distal end 40b of the medial upper housing 22b. The upper distal strap guide member 38a has a strap guide loop 44 and a rotationally-connected strap lock 46 positioned adjacent to the strap guide loop 44. The upper distal strap connection member 42a has a strap anchor loop 48 and a strap connection hook 50 positioned on opposite sides of the upper distal strap connection member 42a.

The upper distal strap guide and connection members 38a, 42a are preferably fabricated from a relatively rigid material, such as a high-strength plastic, and have an arcuate configuration, which corresponds to the contours of the body of the user. The upper distal strap retention assembly 34a further includes an upper distal strap attachment member 52a likewise preferably fabricated from a relatively rigid high-strength plastic. The upper distal strap attachment member 52a has a strap attachment loop 54 and a strap connection loop 56 positioned on opposite sides of the upper distal strap attachment member 52a.

The upper proximal strap retention assembly 36a includes an upper proximal strap guide member 58a attached to a proximal end 60a of the lateral upper support arm 20a by fasteners 62, such as rivets, and an upper proximal strap connection member 64a attached to a proximal end 60b of the medial upper support arm 20b likewise by fasteners 62. The upper proximal strap retention assembly 36a further includes an upper proximal strap attachment member 66a. The upper proximal strap guide member 58a, upper proximal strap connection member 64a, and upper proximal strap attachment member 66a have essentially the same construction as the upper distal strap guide member 38a, upper distal strap connection member 42a, and upper distal strap attachment member 52a, respectively. Accordingly, components common to corresponding members are designated by the same reference characters.

The orthopedic brace 10 still further comprises a lower distal strap retention assembly 34b and a lower proximal strap retention assembly 36b, each of which is associated with both the lateral and medial lower support assemblies 16a, 16b. The lower distal strap retention assembly 34b is essentially the same as the upper distal strap retention assembly 34a. As such, the lower distal strap retention assembly 34b includes a lower distal strap guide member 38b integral with a distal end 68a of the lateral lower housing 26a, a lower distal strap connection member 42b integral with a distal end 68b of the medial lower housing 26b, and a lower distal strap attachment member 52b.

The lower proximal strap retention assembly 36b is essentially the same as the upper proximal strap retention assembly 36a. As such, the lower proximal strap retention assembly 36b includes a lower proximal strap guide member 58b attached to a proximal end 70a of the lateral lower support arm 24a by fasteners 62, a lower proximal strap connection member 64b attached to a proximal end 70b of the medial lower support arm 24b by fasteners 62, and a lower proximal strap attachment member 66b. The lower distal and lower proximal strap guide members 38b, 58b, lower distal and lower proximal strap connection members 42b, 64b, and lower distal and lower proximal strap attachment members 52b, 66b have essentially the same construction as the upper distal and upper proximal strap guide members 38a, 58a, upper distal and upper proximal strap connection members 42a, 64a, and upper distal and upper proximal strap attachment members 52a, 66a, respectively. Accordingly, components common to corresponding members are designated by the same reference characters.

A pad 72 is preferably provided in association with each upper and lower distal strap guide and connection member 38a, 38b, 42a, 42b and each upper and lower proximal strap guide and connection member 58a, 58b, 64a, 64b. The pads 72 are affixed to the inner face of each of the members 38a, 38b, 42a, 42b, 58a, 58b, 64a, 64b by fastening means (not shown), such as hook and loop fasteners commonly termed VELCRO. The pads 72 cushion the body of the user from the relatively hard, rigid surfaces of the orthopedic brace 10 when the orthopedic brace 10 is mounted on the body.

Figure 2:
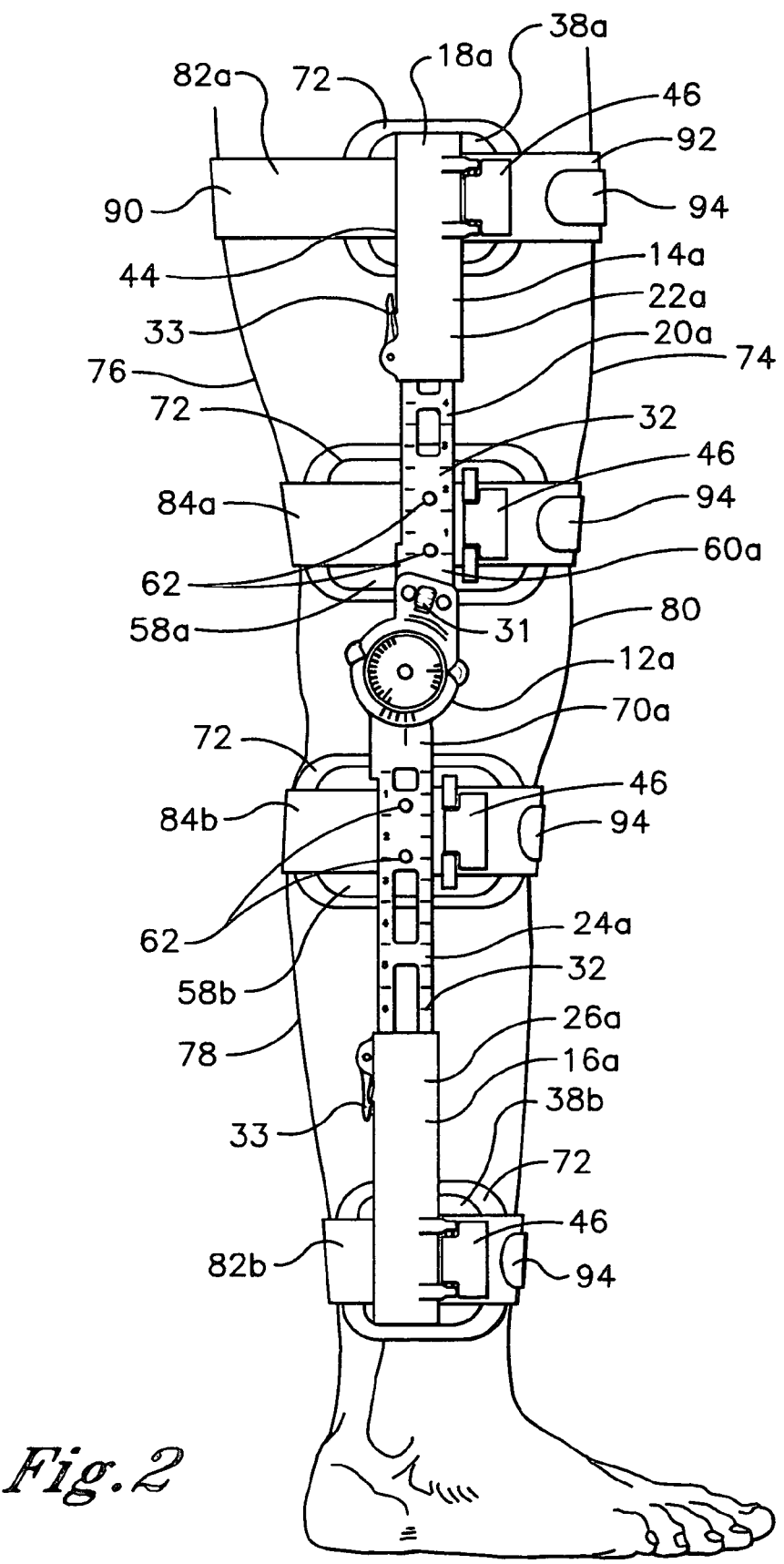
FIG. 2 is a lateral view of the orthopedic brace of FIG. 1 mounted on the leg of a user following the present fitting method.
Figure 3:
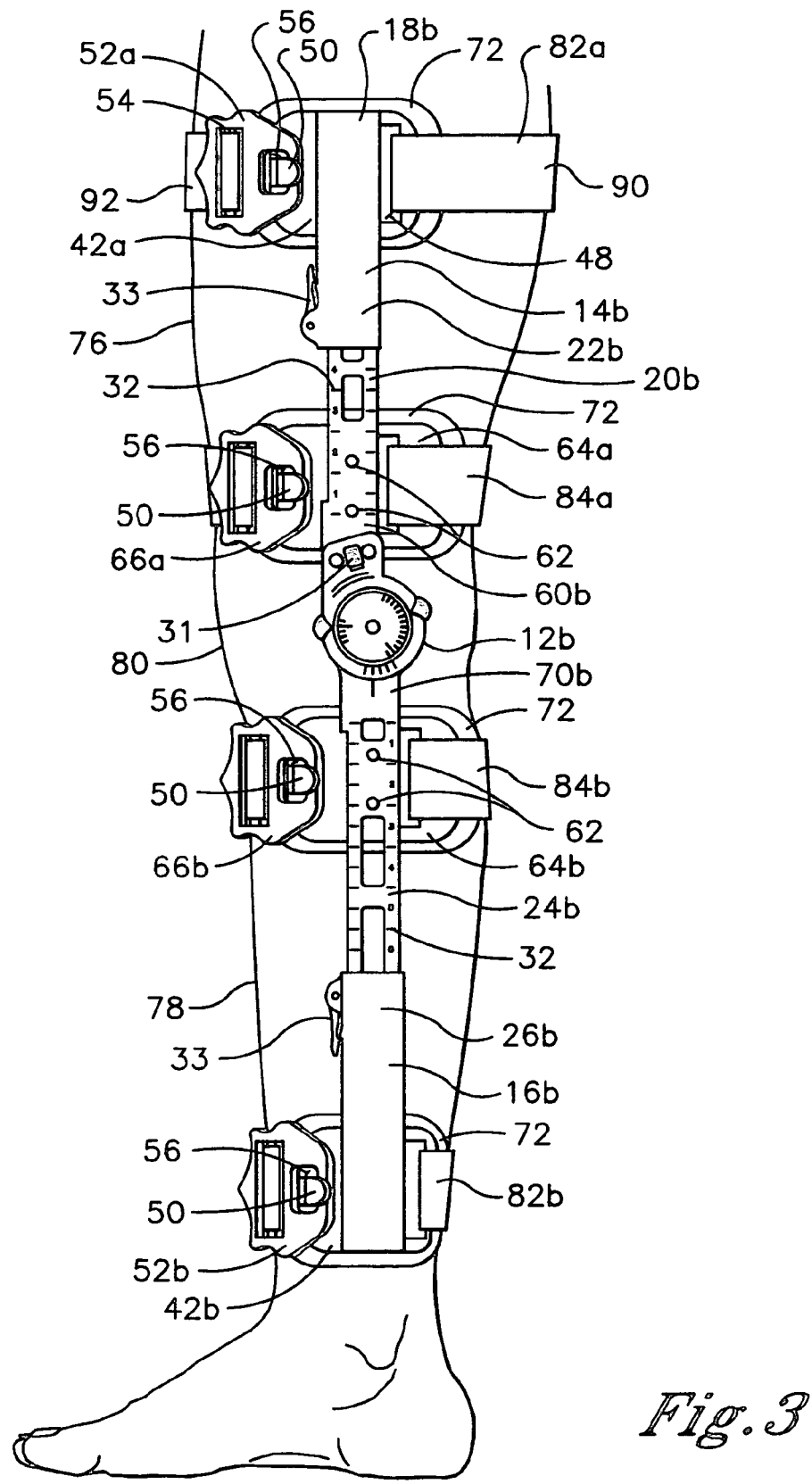
FIG. 3 is a medial view of the orthopedic brace of FIG. 1 mounted on the leg of a user following the present fitting method.

For purposes of illustration, the orthopedic brace 10 is a specific type of orthopedic brace commonly termed a post-operative knee brace. Full utility of the orthopedic brace 10 is achieved when the orthopedic brace 10 is mounted on the leg of a user. Referring additionally to FIGS. 2 and 3, the orthopedic brace 10 is shown mounted on the right leg 74, which is characterized as having an upper leg 76, a lower leg 78, and a knee joint 80 rotationally connecting the upper and lower legs 76, 78. It will be apparent to the skilled artisan that the post-operative knee brace 10 is likewise adaptable for mounting on the left leg (not shown) of the user.

The orthopedic brace 10 is further provided with a plurality of straps which engage the strap retention assemblies to retain the orthopedic brace 10 on the leg 74 during use. In particular, an upper distal strap 82a engages the upper distal strap retention assembly 34a and an upper proximal strap 84a engages the upper proximal strap retention assembly 36a. A lower distal strap 82b similarly engages the lower distal strap retention assembly 34b and a lower proximal strap 84b engages the lower proximal strap retention assembly 36b.

Engagement of the upper distal strap 82a with the upper distal strap retention assembly 34a is effected by anchoring a first end 86 of the upper distal strap 82a to the strap anchor loop 48 of the upper distal strap connection member 42a by relatively permanent fastening means, such as sewing. The second end 88 of the upper distal strap 82a is threaded through the strap guide loop 44 of the upper distal strap guide member 38a to define a posterior segment 90 of the upper distal strap 82a, which extends between the upper distal strap connection member 42a and upper distal strap guide member 38a. As such, the posterior segment 90 posteriorly connects the lateral and medial longitudinal brace assemblies 18a, 18b.

The second end 88 of the upper distal strap 82a passes through the upper distal strap guide member 38a and is threaded into the strap attachment loop 54 of the upper distal strap attachment member 52a to define an anterior segment 92 of the upper distal strap 82a which extends between the upper distal strap guide member 38a and upper distal strap attachment member 52a. A second end segment 91 of the upper distal strap 82a is correspondingly defined, which is the segment of the upper distal strap 82a which extends from the upper distal strap attachment member 52a to the free second end 88 of the upper distal strap 82a.

The strap connection loop 56 of the upper distal strap attachment member 52a is coupled with the strap connection hook 50 of the upper distal strap connection member 42a so that the anterior segment 92 of the upper distal strap 82a anteriorly connects the lateral and medial longitudinal brace assemblies 18a, 18b. Thus, the posterior and anterior segments 90, 92 of the upper distal strap 82a in combination (exclusive of the second end segment 91) completely encircle the leg 74 when the orthopedic brace 10 is mounted on the leg 74. The posterior and anterior segments 90, 92 of the upper distal strap 82a in combination are termed the encircling segment. A fastening tab 94 is releasably attached to the second end 88 and provides fastening means, such as hook and loop fasteners, for releasably fastening the free second end 88 extending from the strap attachment loop 54 back onto the upper distal strap 82a.

Engagement of the lower distal strap 82b with the lower distal strap retention assembly 34b, the upper proximal strap 84a with the upper proximal strap retention assembly 36a, and the lower proximal strap 84b with the lower proximal strap retention assembly 36b is effected in an essentially similar manner as described above with respect to the upper distal strap 82a and upper distal strap retention assembly 34a. As such, the upper distal strap 82a, lower distal strap 82b, upper proximal strap 84a, and lower proximal strap 84b closely secure the orthopedic brace 10 to the leg 74 of the user.

When the orthopedic brace 10 is properly mounted on and closely secured to the leg 74, the lateral central joint 12a is positioned adjacent to the lateral side of the knee joint 80 and the medial central joint 12b is positioned adjacent to the medial side of the knee joint 80. The lateral upper longitudinal support assembly 14a is positioned adjacent to the lateral side of the upper leg 76 is longitudinally aligned with the lateral side of the upper leg 76. The medial upper longitudinal support assembly 14b is positioned adjacent to the medial side of the upper leg 76 and is longitudinally aligned with the medial side of the upper leg 76. The lateral lower longitudinal support assembly 16a is similarly positioned adjacent to the lateral side of the lower leg 78 and is longitudinally aligned with the lateral side of the lower leg 78. The medial lower longitudinal support assembly 16b is positioned adjacent to the medial side of the lower leg 78 and is longitudinally aligned with the medial side of the lower leg 78.

Although the brace components have been described above for purposes of illustration as applying to a post-operative knee brace, it is apparent from the foregoing that the above-recited brace components are readily adaptable to other types of orthopedic braces for the knee or other joints or regions of the body in addition to post-operative knee braces. It is additionally noted that each set of upper support arm, central joint, and lower support arm in the embodiment of the post-operative knee brace described above is a series of discrete interconnected components. However, in accordance with an alternate embodiment of the present invention not shown, either the upper support arm or the lower support arm can be integrally formed with the central joint as a continuous structure, which cooperatively functions with the remaining non-integrated support arm.

In accordance with another alternate embodiment of the present invention not shown, the position of any housing and correspondingly paired support arm can be reversed so that the upper housing and/or lower housing is more proximal to the central joint than the correspondingly paired upper and/or lower support arm. As such the housing, rather than the correspondingly paired support arm, is attached to or integral with the central joint. However, the support arm remains slidably displaceable within the housing. In accordance with yet another alternate embodiment of the present invention not shown, the upper support arm, central joint, and lower support arm (or alternatively upper housing, central joint, and lower housing) can be integrally formed together as a single continuous static structure, wherein the resulting orthopedic brace functions as a rigid splint having support assemblies with an adjustable length.

Figure 4:
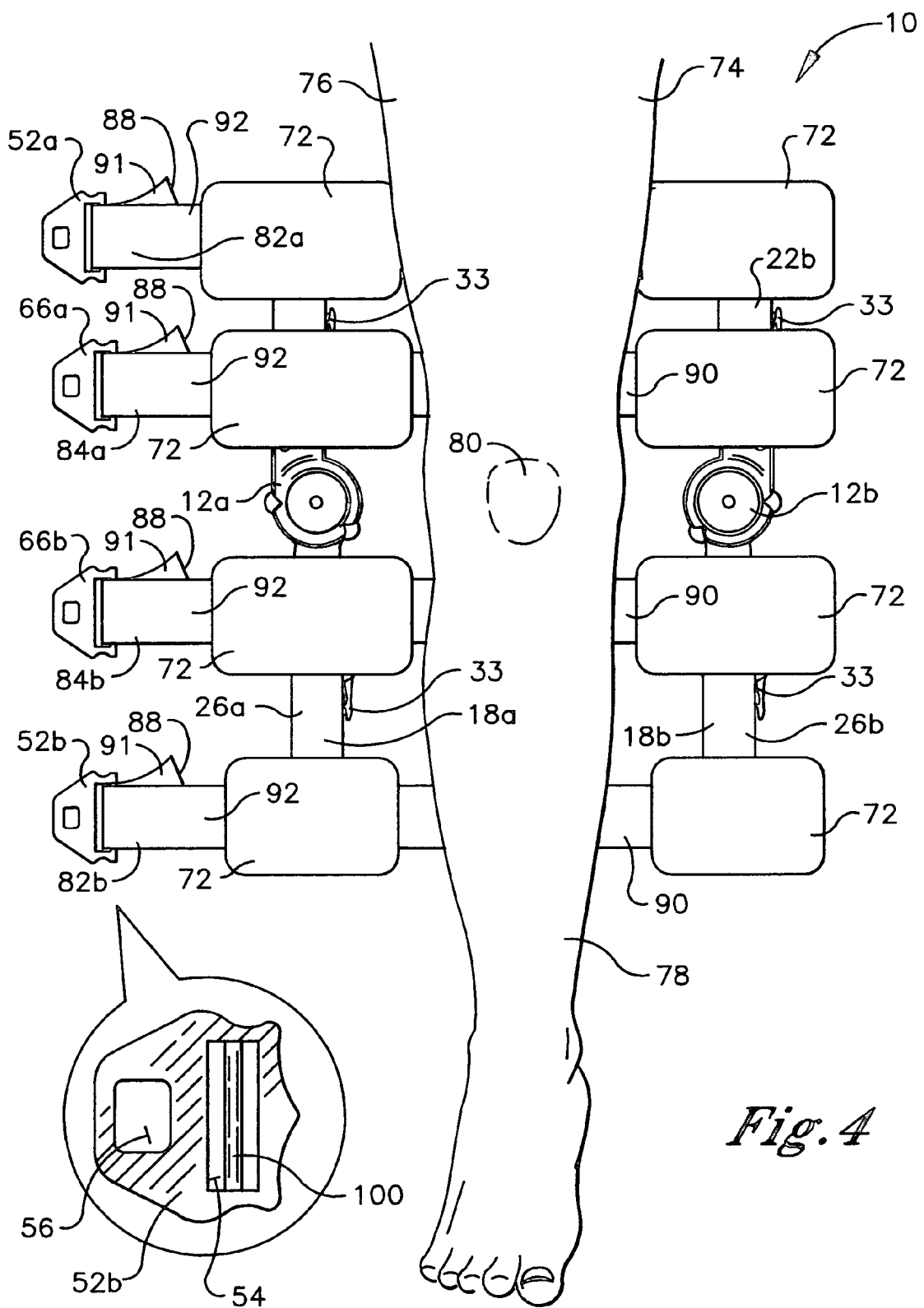
FIG. 4 is a front view of the orthopedic brace of FIG. 1 in a laid out position following a laying out step of the present fitting method.

A method for fitting the orthopedic brace 10 to the leg 74 of a user is described below with reference to FIGS. 4-11. The method is initiated by a laying out step. FIG. 4 shows the orthopedic brace 10 in a laid out position after completion of the laying out step. The practitioner has slidably engaged the anterior segments 92 with the associated strap guide members 38a, 38b, 58a, 58b and attached the anterior segments 92 of the straps 82a, 82b, 84a, 84b to the strap attachment members 52a, 52b, 66a, 66b to set the anterior segments 92 at an arbitrary length. Attachment is effected by threading the second ends 88 of each strap 82a, 82b, 84a, 84b into the strap attachment loop 54 of the associated strap attachment members 52a, 52b, 66a, 66b, threading the second end 88 around a strap post 100 extending across the strap attachment loop 54, and threading the second end 88 back out the strap attachment loop 54.

The practitioner has maintained all the strap connection loops 56 on the strap attachment members 52a, 52b, 66a, 66b uncoupled from their associated strap connection hooks 50 on the strap connection members 42a, 42b, 64a, 64b. In addition, all the strap locks 46 mounted on the strap guide members 38a, 38b, 58a, 58b are maintained in an open or unlocked position so that the strap locks 46 are disengaged from their associated straps 82a, 82b, 84a, 84b. The lock levers 33 are conversely maintained in the closed position. (Note that the strap connection hooks 50, strap connection members 42a, 42b, 64a, 64b, strap locks 46, and strap guide members 38a, 38b, 58a, 58b are not visible in the view of FIG. 4, but are visible in the view of FIG. 5 which is described below.)

The practitioner has spread out the orthopedic brace 10 with the inner faces of the lateral and medial central joints 12a, 12b and the inner faces of the pads 72 fastened to the strap guide members 38a, 38b, 58a, 58b and strap connection members 42a, 42b, 64a, 64b exposed. The lateral and medial longitudinal brace assemblies 18a, 18b are posteriorly connected to one another by the posterior segments 90 of the straps 82a, 82b, 84a, 84b, which slidably engage the associated strap guide members 38a, 38b, 58a, 58b and which are fixably attached to the associated strap connection members 42a, 42b, 64a, 64b at the first end 86 to set the posterior segments 90 at an arbitrary length.

Although the anterior segments 92 slidably engage the associated strap guide members 38a, 38b, 58a, 58b as recited above, the anterior segments 92 are disconnected from the associated strap connection members 42a, 42b, 64a, 64b so that the lateral and medial longitudinal brace assemblies 18a, 18b are anteriorly disconnected from one another. The second end segments 91 and anterior segments 92 of the straps 82a, 82b, 84a, 84b are unfurled and the second ends 88 of the straps 82a, 82b, 84a, 84b are free. The lateral and medial longitudinal brace assemblies 18a, 18b are essentially parallely positioned a spaced distance apart from one another, which approximates the width of the leg 74. The leg 74 is anteriorly positioned (relative to the posterior segments 90) between the lateral and medial longitudinal brace assemblies 18a, 18b and the knee joint 80 is aligned with the lateral and medial central joints 12a, 12b.

Figure 5:
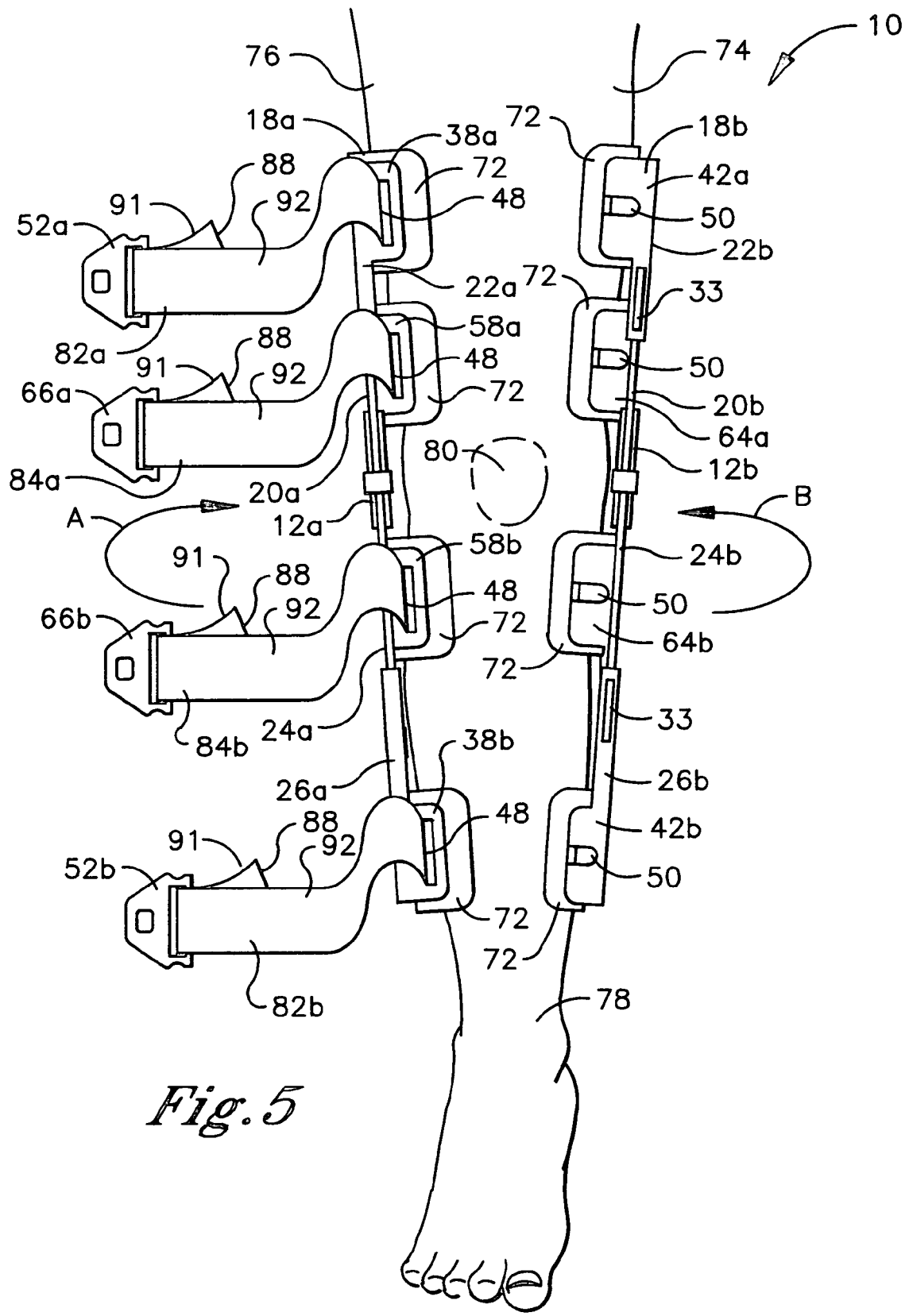
FIG. 5 is a front view of the orthopedic brace of FIG. 1 in a leg engaged position following a leg engaging step of the present fitting method.

The present fitting method further comprises a leg engaging step. FIG. 5 shows the orthopedic brace 10 in a leg engaged position after completion of the leg engaging step. The practitioner has rotated the lateral longitudinal brace assembly 18a about the posterior segments 90 of the straps 82a, 82b, 84a, 84b in the clockwise direction of arrow A toward the leg 74 and similarly rotated the lateral longitudinal brace assembly 18b about the posterior segments 90 in the counter-clockwise direction of arrow B. Rotation of the lateral and medial longitudinal brace assemblies 18a, 18b toward the leg 74 brings the pads 72 affixed to the upper distal and proximal strap guide members 38a, 58a into close-fitting engagement with the lateral side of the upper leg 76, the pads 72 affixed to the upper distal and proximal strap connection members 42a, 64a into close-fitting engagement with the medial side of the upper leg 76, the pads 72 affixed to the lower distal and proximal strap guide members 38b, 58b into close-fitting engagement with the lateral side of the lower leg 78, and the pads 72 affixed to the lower distal and proximal strap connection members 42b, 64b into close-fitting engagement with the medial side of the lower leg 78. The lateral central joint 12a is also positioned adjacent to the lateral side of the knee joint 80 and the medial central joint 12b is positioned adjacent to the medial side of the knee joint 80. Although not shown, condyle pads may be affixed to the inner faces of the lateral and medial central joints 12a, 12b, which close-fittingly engage the lateral and medial sides of the knee joint 80, respectively.

Figure 6:
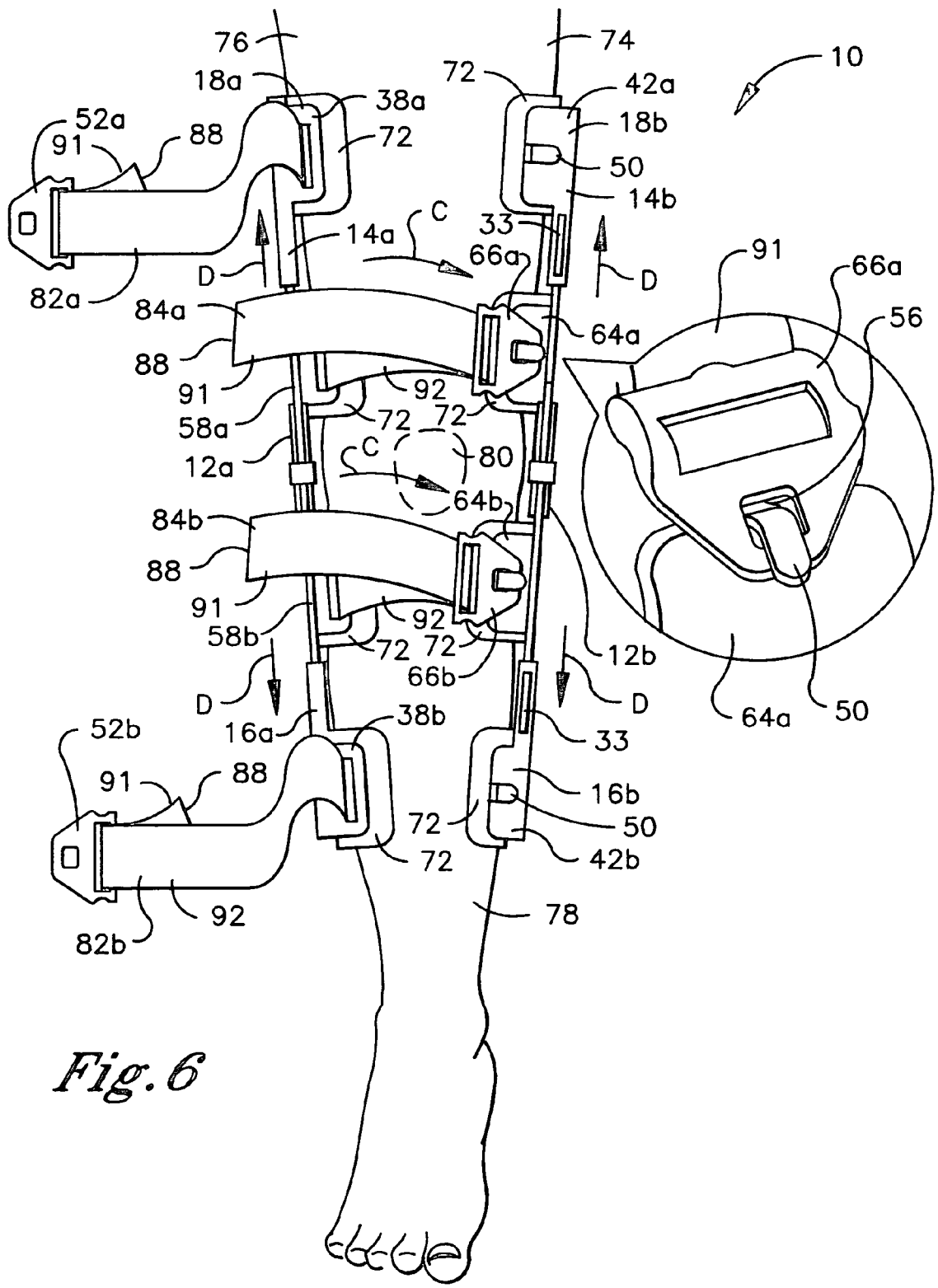
FIG. 6 is a front view of the orthopedic brace of FIG. 1 in a length adjusted position following a length adjusting step of the present fitting method.

The present fitting method further comprises a length adjusting step. FIG. 6 shows the orthopedic brace 10 in a length adjusted position after completion of the length adjusting step. The practitioner has drawn the second ends 88 of the upper and lower proximal straps 84a, 84b in the clockwise direction of arrows C across the anterior of the leg 70 proximally above and below the knee joint 80 until the upper and lower proximal strap attachment members 66a, 66b are adjacent to the upper and lower proximal strap connection members 64a, 64b, respectively. The strap connection loops 56 of the upper and lower proximal strap attachment members 66a, 66b have been coupled with the strap connection hooks 50 of the upper and lower proximal strap connection members 64a, 64b, respectively, so that the anterior segments 92 of the upper and lower proximal straps 84a, 84b loosely anteriorly connect the lateral and medial longitudinal brace assemblies 18*a*, 18*b* to one another proximal to the knee joint 80.

It is noted that the present method is not limited to a specific sequence of coupling the individual strap connection loops 56 with their respective strap connection hooks 50. Thus, it is within the scope of the present method to simultaneously couple the strap connection loops 56 of the upper and lower proximal strap attachment members 66*a*, 66*b* with the strap connection hooks 50 of the upper and lower proximal strap connection members 64*a*, 64*b*. Alternatively, it is within the scope of the present method to first couple the strap connection loop 56 of the upper proximal strap attachment member 66*a* with the strap connection hook 50 of the upper proximal strap connection member 64*a* and thereafter couple the strap connection loop 56 of the lower proximal strap attachment member 66*b* with the strap connection hook 50 of the lower proximal strap connection member 64*b*. In another alternative, it is within the scope of the present method to first couple the strap connection loop 56 of the lower proximal strap attachment member 66*b* with the strap connection hook 50 of the lower proximal strap connection member 64*b* and thereafter couple the strap connection loop 56 of the upper proximal strap attachment member 66*a* with the strap connection hook 50 of the upper proximal strap connection member 64*a*.

Once the lateral and medial longitudinal brace assemblies 18*a*, 18*b* are anteriorly proximally connected to one another, the length adjusting step proceeds by transitioning the lock levers 33 from the closed position to the open position and adjusting the length of the lateral and medial upper and lower support assemblies 14*a*, 14*b*, 16*a*, 16*b* upward or downward in the direction of arrows D as desired in correspondence with the dimensions of the leg 74 of the user. The lock levers 33 are then returned to the closed position.

Figure 7:
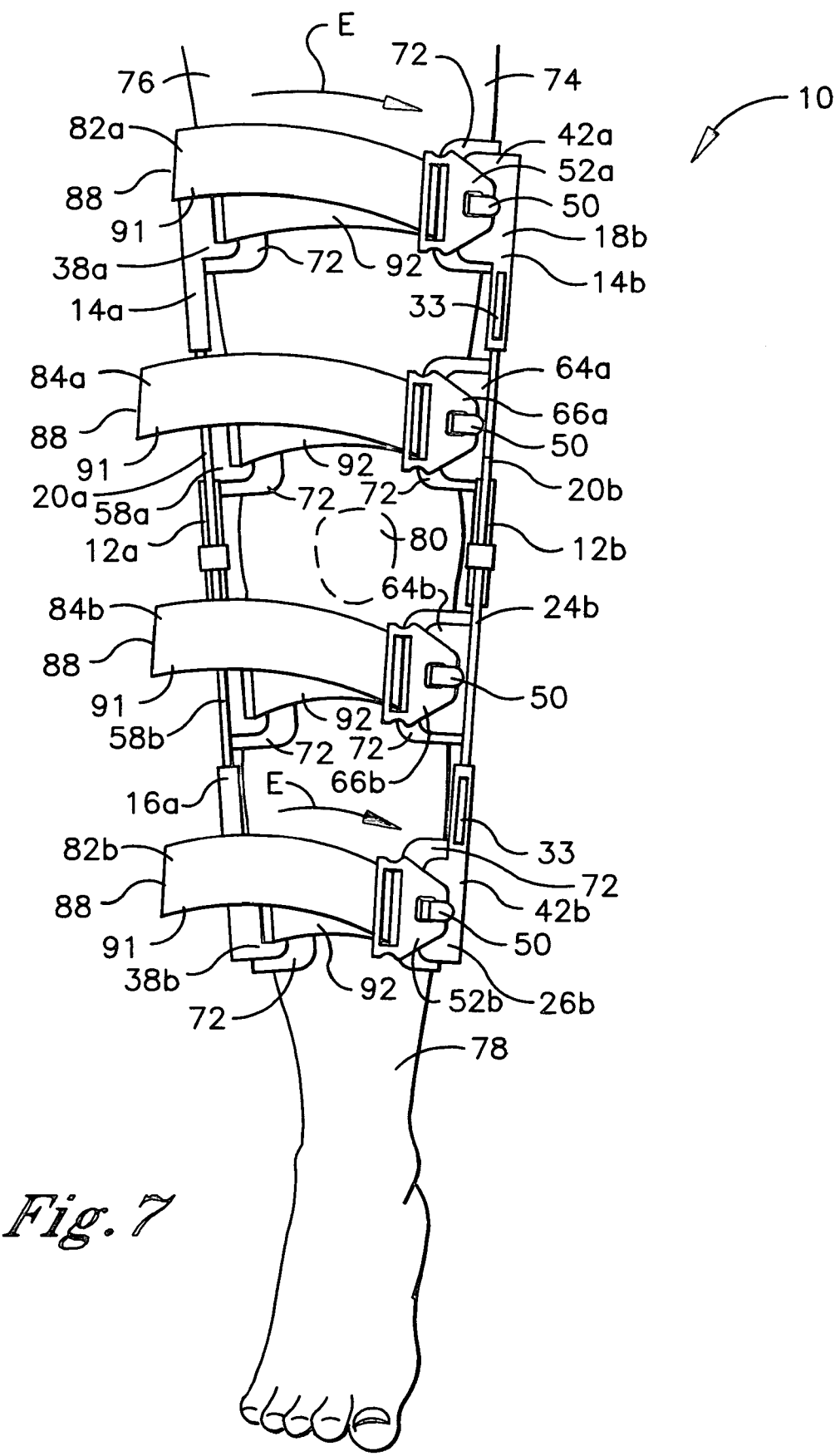
FIG. 7 is a front view of the orthopedic brace of FIG. 1 in a strap connected position following a strap connecting step of the present fitting method.

The present fitting method further comprises a strap connecting step. FIG. 7 shows the orthopedic brace 10 in a strap connected position after completion of the strap connecting step. The practitioner has drawn the second ends 88 of the upper and lower distal straps 82*a*, 82*b* in the clockwise direction of arrows E across the anterior of the leg 70 distally above and below the knee joint 80 until the upper and lower distal strap attachment members 52*a*, 52*b* are adjacent to the upper and lower distal strap connection members 42*a*, 42*b*, respectively. The strap connection loops 56 of the upper and lower distal strap attachment members 52*a*, 52*b* have been coupled with the strap connection hooks 50 of the upper and lower distal strap connection members 42*a*, 42*b*, respectively, so that the anterior segments 92 of the upper and lower distal straps 82*a*, 82*b* loosely anteriorly connect the lateral and medial longitudinal brace assemblies 18*a*, 18*b* to one another distal to the knee joint 80 in essentially the same manner that the upper and lower proximal straps 84*a*, 84*b* connect the lateral and medial longitudinal brace assemblies 18*a*, 18*b* proximal to the knee joint 80.

In accordance with an alternate embodiment not shown, the length adjusting and strap connecting steps recited above are modified to change the overall sequence of anteriorly connecting the lateral and medial longitudinal brace assemblies 18*a*, 18*b* to one another and adjusting the length of the lateral and medial upper and lower support assemblies 14*a*, 14*b*, 16*a*, 16*b*. In particular, the alternate length adjusting step omits the actions of drawing the second ends 88 of the upper and lower proximal straps 84*a*, 84*b* across the anterior of the leg 70 and coupling the strap connection loops 56 of the upper and lower proximal strap attachment members 66*a*, 66*b* with the strap connection hooks 50 of the upper and lower proximal strap connection members 64*a*, 64*b*. The alternate length adjusting step comprises transitioning the lock levers 33 from the closed position to the open position, adjusting the length of the lateral and medial upper and lower support assemblies 14*a*, 14*b*, 16*a*, 16*b* upward or downward as desired, and returning the lock levers 33 to the closed position, while all the anterior segments 92 of the upper and lower distal and proximal straps 82*a*, 82*b*, 84*a*, 84*b* remain disconnected from the medial longitudinal brace assembly 18*b*.

The alternate strap connecting step includes the actions omitted from the alternate length adjusting step recited above. In particular, the alternate strap connecting step comprises drawing the second ends 88 of the upper and lower proximal straps 84*a*, 84*b* across the anterior of the leg 70 and coupling the strap connection loops 56 of the upper and lower proximal strap attachment members 66*a*, 66*b* with the strap connection hooks 50 of the upper and lower proximal strap connection members 64*a*, 64*b*. The alternate strap connecting step further comprises likewise drawing the second ends 88 of the upper and lower distal straps 82*a*, 82*b* across the anterior of the leg 70 and coupling the strap connection loops 56 of the upper and lower distal strap attachment members 52*a*, 52*b* with the strap connection hooks 50 of the upper and lower distal strap connection members 42*a*, 42*b*. As noted above, the present method is not limited to a specific sequence of coupling the individual strap connection loops 56 with their respective strap connection hooks 50. Thus, it within the scope of the present method to connect the strap connection loops 56 of the upper and lower distal and proximal strap attachment members 52*a*, 52*b*, 66*a*, 66*b* with the corresponding strap connection hooks 50 of the upper and lower distal and proximal strap connection members 42*a*, 42*b*, 64*a*, 64*b*, simultaneously or in essentially any sequence.

Figure 8:
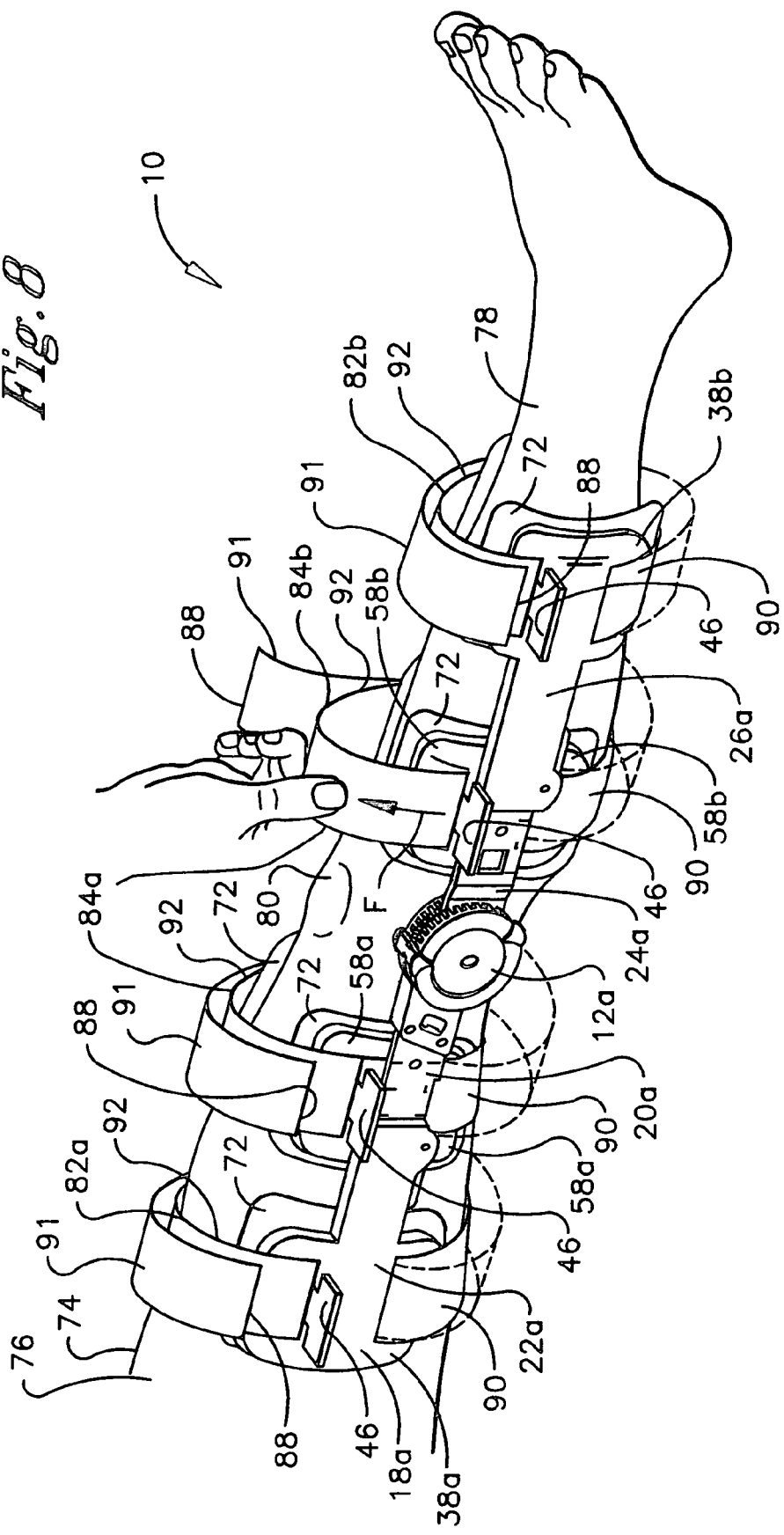
FIG. 8 is a lateral view of the orthopedic brace of FIG. 1 in a posterior segment tensioned position following a posterior segment tensioning step of the present fitting method.

In any case, the present fitting method further comprises a posterior segment tensioning step. FIG. 8 shows the orthopedic brace 10 in a posterior segment tensioned position after completion of the posterior segment tensioning step. The practitioner has drawn the anterior segments 92 of the upper and lower distal and proximal straps 82*a*, 82*b*, 84*a*, 84*b* in the outward direction of arrow F away from the anterior of the leg 70 without substantially displacing the lateral and medial longitudinal brace assemblies 18*a*, 18*b* relative to the leg 70. The upper and lower distal and proximal straps 82*a*, 82*b*, 84*a*, 84*b* have been slid through the upper and lower distal and proximal strap guide members 38*a*, 38*b*, 58*a*, 58*b*, respectively, while the first ends 86 of the upper and lower distal and proximal straps 82*a*, 82*b*, 84*a*, 84*b* remain anchored to the strap anchor loops 48 of the upper and lower distal and proximal strap connection members 42*a*, 42*b*, 64*a*, 64*b*. As a result, the posterior segments 90 of the upper and lower distal and proximal straps 82*a*, 82*b*, 84*a*, 84*b* have been pulled taut against the posterior of the leg 70.

Figure 9:
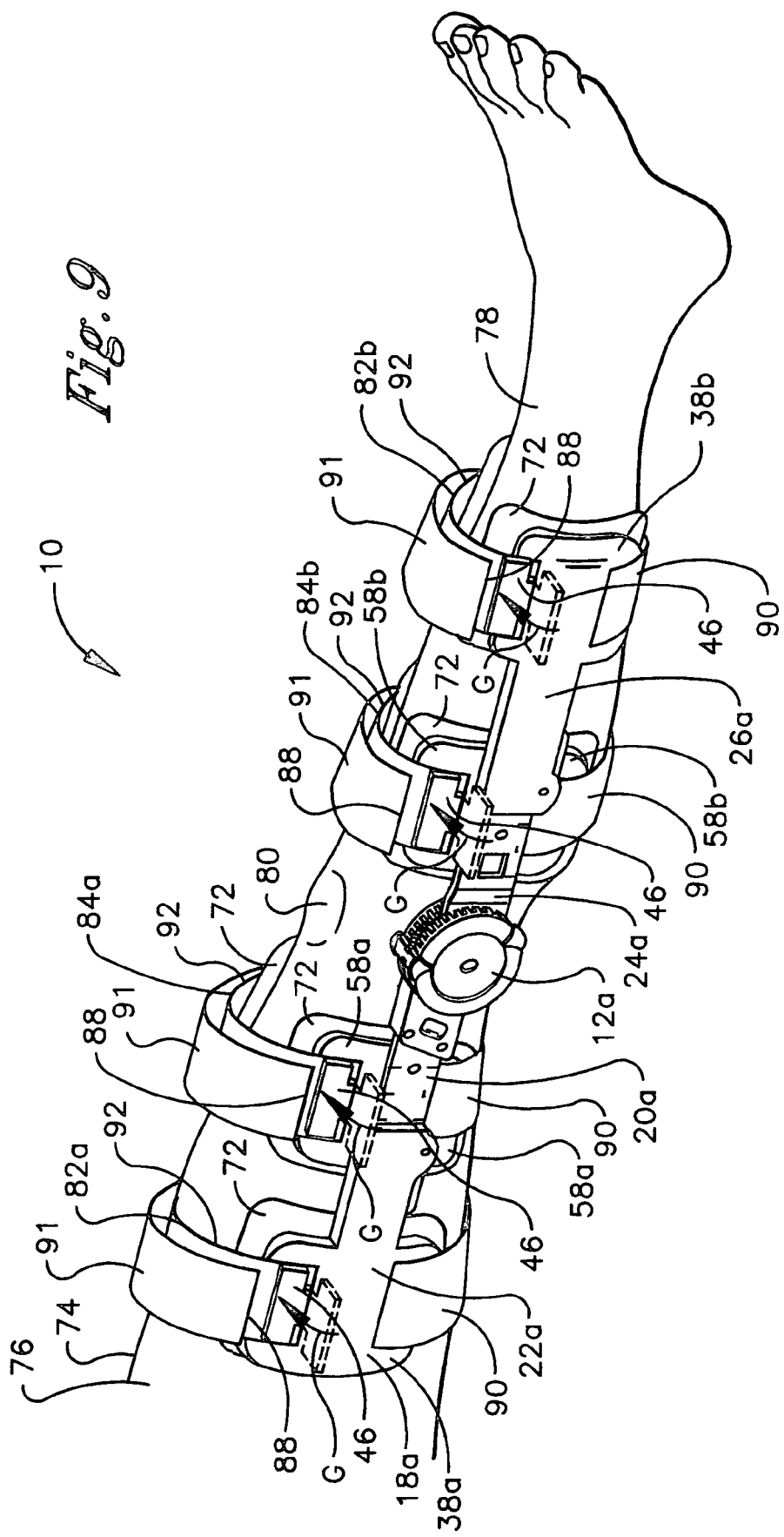
FIG. 9 is a lateral view of the orthopedic brace of FIG. 1 in a strap locked position following a strap locking step of the present fitting method.

The present fitting method further comprises a strap locking step. FIG. 9 shows the orthopedic brace 10 in a strap locked position after completion of the strap locking step. The practitioner has transitioned each of the strap locks 46 mounted on the strap guide members 38*a*, 38*b*, 58*a*, 58*b* from the open position to a closed or locked position, thereby changing the posterior segment 90 of each upper and lower distal and proximal strap 82*a*, 82*b*, 84*a*, 84*b* from the arbitrary length and essentially fixing the posterior segment at a desired fixed length. The closed position of the strap locks 46 has been effected by rotating each strap lock 46 in the clockwise direction of arrows G until the strap lock 46 engages the outer face of its associated upper and lower distal and proximal strap 82*a*, 82*b*, 84*a*, 84*b*. The strap locks 46 are releasably fastened to the upper and lower distal and proximal straps 82*a*, 82*b*, 84*a*, 84*b* by hook and loop fasteners mounted on the inner face of each strap lock 46 and on the outer face of each upper and lower distal and proximal strap 82*a*, 82*b*, 84*a*, 84*b*.

Figure 10:
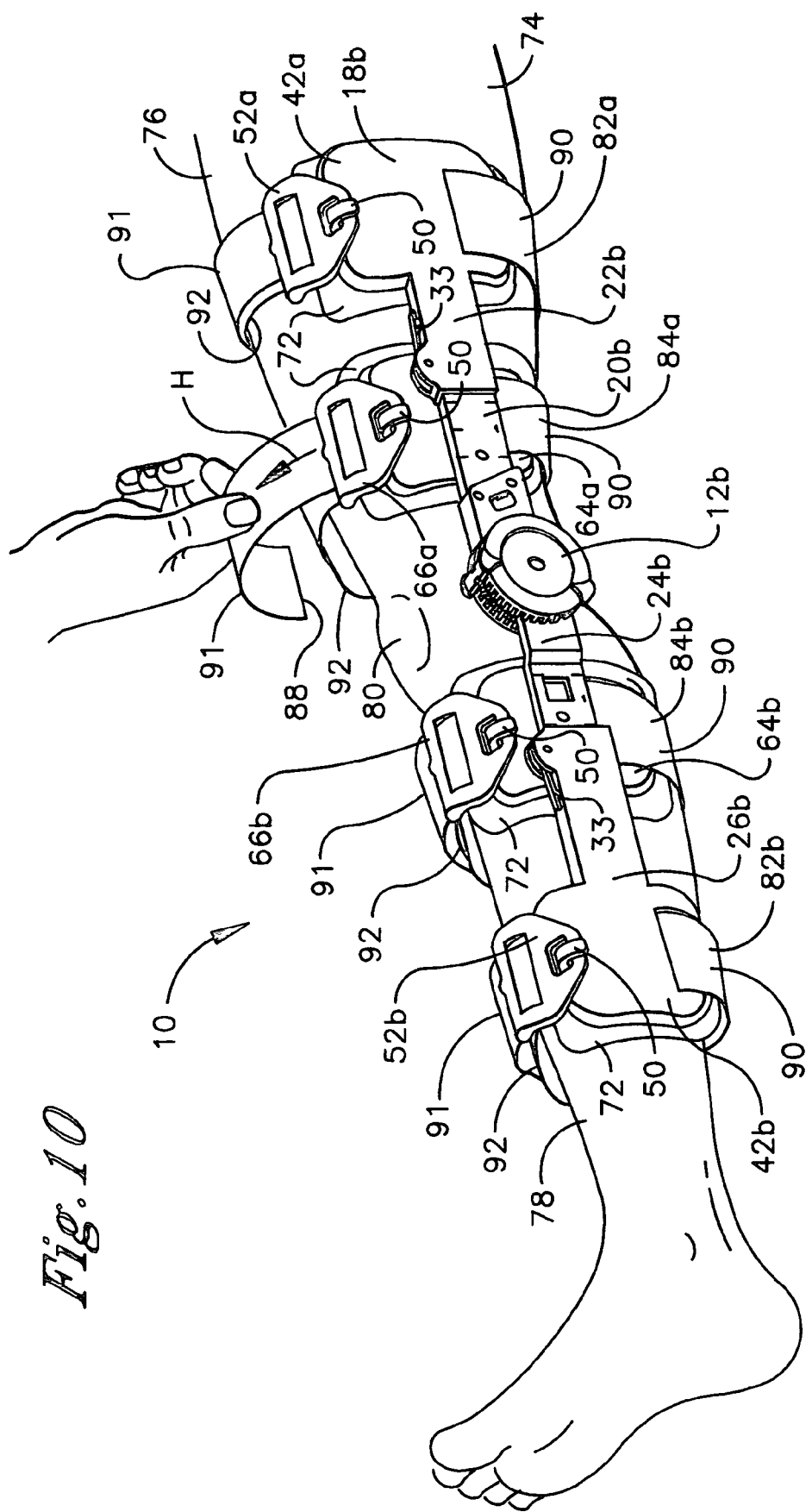
FIG. 10 is a medial view of the orthopedic brace of FIG. 1 in an anterior segment tensioned position following a anterior segment tensioning step of the present fitting method.

The present fitting method further comprises an anterior segment tensioning step. FIG. 10 shows the orthopedic brace 10 in an anterior segment tensioned position after completion of the anterior segment tensioning step. The practitioner has drawn the second ends 88 of the upper and lower distal and proximal straps 82*a*, 82*b*, 84*a*, 84*b* in the counter-clockwise direction of arrow H across the anterior of the leg 70. The anterior segments 92 of the upper and lower distal and proximal straps 82*a*, 82*b*, 84*a*, 84*b* have been slid around the strap posts 100 in the strap attachment loops 54 of the upper and lower distal and proximal strap attachment members 52*a*, 52*b*, 66*a*, 66*b*, respectively, while the strap connection loops 56 remain coupled with the strap connection hooks 50 of the upper and lower distal and proximal strap connection members 42*a*, 42*b*, 64*a*, 64*b*. As a result, the anterior segments 92 of the upper and lower distal and proximal straps 82*a*, 82*b*, 84*a*, 84*b* have been pulled taut against the anterior of the leg 70. Each anterior segment 92 has been changed from the arbitrary length and essentially fixed at a desired fixed length. Since the length of the posterior segments 90 has been previously fixed in the strap locking step, the length of the encircling segment 90, 92 is likewise fixed by the anterior tensioning step.

Figure 11:
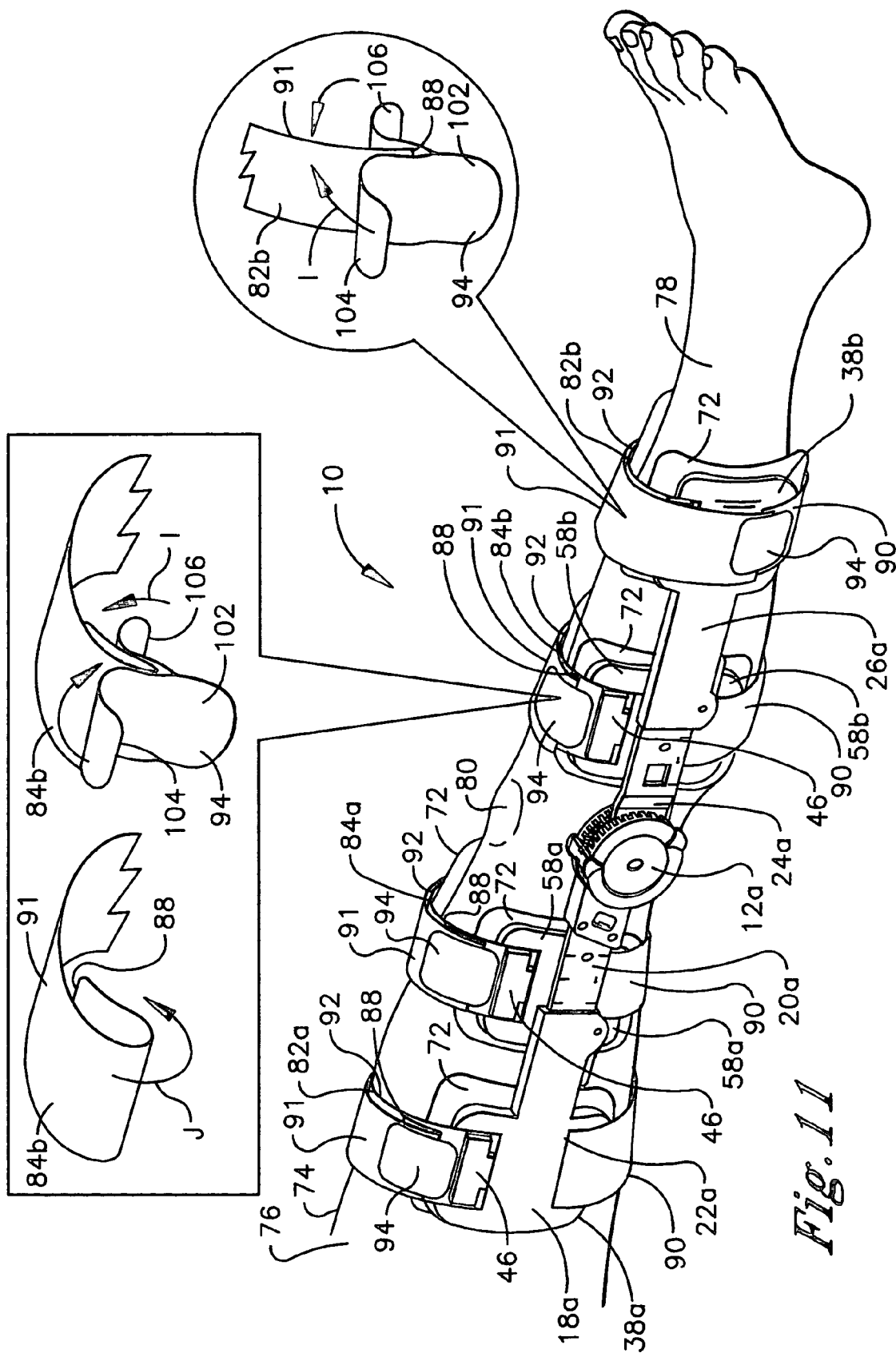
FIG. 11 is a lateral view of the orthopedic brace of FIG. 1 in a strap end secured position following a strap end securing step of the present fitting method.

The present fitting method further comprises a strap end securing step. FIG. 11 shows the orthopedic brace 10 in a strap end secured position after completion of the strap securing step. The practitioner has fastened the second end 88 of each upper and lower distal and proximal strap 82*a*, 82*b*, 84*a*, 84*b* onto its associated anterior segment 92 by means of the fastening tab 94. The fastening tabs 94 are Y-shaped, each having a primary segment 102, a first bifurcated segment 104, and a second bifurcated segment 106. The fastening tab 94 has been fastened to the second end 88 by placing the second end 88 between the separated first and second bifurcated segments 104, 106 of the fastening tab 94 and pressing the first and second bifurcated segments 104, 106 together in the direction of arrows I against the opposite faces of the second end 88. Hook and loop fasteners are provided on the inner faces of the first and second bifurcated segments 104, 106 and the opposite faces of the second end 88 to retain the contacted faces in engagement with one another.

The fastening tab 94 has been fastened to the anterior segment 92 of each associated upper and lower distal and proximal strap 82*a*, 82*b*, 84*a*, 84*b* by pressing the inner face of the primary segment 102 against the outer faces of the anterior segment 92. Hook and loop fasteners are provided on the inner face of the primary segment 102 and the outer face of the anterior segment 92 to retain the contacted faces in engagement with one another. It is apparent from FIG. 11 that the practitioner can optionally fold over the second end 88 in the direction of arrow J as shown before fastening the second end 88 to the fastening tab 94 to shorten the length of the second end segment 91 as desired.

The fitting method of the present invention is described above as a sequence of steps, each of which can include of a number of actions. However, not every step or action recited above is necessary to the practice of the fitting method. For example, the fitting method can be practiced in the absence of adjusting the length of the lateral and medial upper and lower support assemblies 14*a*, 14*b*, 16*a*, 16*b* and/or in the absence of securing the second ends 88 of the upper and lower distal and proximal straps 82*a*, 82*b*, 84*a*, 84*b*. In addition, the fitting method is not limited to performing the steps and/or their inclusive actions in the specific sequence recited above.

The present fitting method is particularly advantageous because it enables the practitioner to remove the orthopedic brace 10 from the leg 74 of the user and remount the orthopedic brace 10 on the same leg 74 at a later time without changing the length of the encircling segment 90, 92 of any of the straps 82*a*, 82*b*, 84*a*, 84*b*. As a result, once the orthopedic brace 10 has been initially fitted on the leg 74 in accordance with the above-recited method, the necessity of readjusting the strap lengths every time the orthopedic brace 10 is removed and remounted on the leg 74 is generally avoided.

Removal of the orthopedic brace 10 from the leg 74 while the orthopedic brace 10 is in the strap end secured position is readily effected simply by uncoupling each of the strap connection loops 56 of the upper and lower distal and proximal strap attachment members 52*a*, 52*b*, 66*a*, 66*b* from the strap connection hooks 50 of the upper and lower distal and proximal strap connection members 42*a*, 42*b*, 64*a*, 64*b*. The orthopedic brace 10 is then placed in the laid out position without altering the length of any of the encircling segments 90, 92 and the leg 74 is withdrawn from the orthopedic brace 10.

Remounting the orthopedic brace 10 on the leg 74 is readily effected simply by placing the orthopedic brace 10 in the leg engaging position and recoupling each of the strap connection loops 56 of the upper and lower distal and proximal strap attachment members 52*a*, 52*b*, 66*a*, 66*b* with the strap connection hooks 50 of the upper and lower distal and proximal strap connection members 42*a*, 42*b*, 64*a*, 64*b*. Thus, the orthopedic brace 10 is returned to the strap end secured position without having altered the length of any of the encircling segments 90, 92 during remounting of the orthopedic brace 10.

The present fitting method is additionally advantageous because it enables the practitioner to readjust the position of the orthopedic brace 10 on the leg 74 while the orthopedic brace 10 remains mounted on the leg 74 and without anteriorly disconnecting the lateral and medial longitudinal brace assemblies 18*a*, 18*b* from one another or without changing the length of the encircling segment 90, 92 of any of the straps 82*a*, 82*b*, 84*a*, 84*b*. This position readjusting step has particularly utility when the dimensions of the leg 74 are variable over time due to increased or decreased swelling of the leg 74 or due removal or application of bandages to the leg 74. The position readjusting step is enabled because the straps 82*a*, 82*b*, 84*a*, 84*b* are never directly attached to the lateral longitudinal brace assembly 18*a*, but are only indirectly fixably connected to the lateral longitudinal brace assembly 18*a* by means of the releasably closed strap locks 46, which are in turn rotatably attached to the lateral longitudinal brace assembly 18*a*.

If the practitioner wishes to modify the position of the lateral and medial longitudinal brace assemblies 18*a*, 18*b* relative to the leg 74, the practitioner performs the position readjusting step simply by rotating the strap locks 46 from the closed to the open position. The practitioner can then freely displace either the lateral longitudinal brace assembly 18*a*, the medial longitudinal brace assembly 18*b*, or both assemblies 18*a*, 18*b* about the leg 74, preferably in a rotational direction, independent of the straps 82*a*, 82*b*, 84*a*, 84*b* to a more desired position while the orthopedic brace 10 remains mounted on the leg 74. It is noted that although the length of each encircling segment 90, 92 of the straps 82*a*, 82*b*, 84*a*, 84*b* remains unchanged during the position readjusting step, the individual desired fixed length of each posterior and anterior segment 90, 92 of the straps 82*a*, 82*b*, 84*a*, 84*b* is changed to a readjusted fixed length during the position readjusting step.

While the forgoing preferred embodiments of the invention have been described and shown, it is understood that alternatives and modifications, such as those suggested and others, may be made thereto and fall within the scope of the invention. For example, although the present invention has been described above for purposes of illustration as a method for fitting a post-operative knee brace to the leg, it is apparent from the teaching herein that the present method is readily adaptable for fitting an orthopedic brace to other limbs or regions of the body.

I claim:

1. A method for fitting an orthopedic brace to a body section of a user comprising the steps of:

providing an orthopedic brace including a first longitudinal brace assembly, a second longitudinal brace assembly, a first strap, a second strap, a third strap, a fourth strap, a first strap attachment member, a second strap attachment member, a third strap attachment member, and a fourth strap attachment member, wherein said first longitudinal brace assembly has a first strap guide member, a second strap guide member, a third strap guide member and a fourth strap guide member mounted thereon, each said first, second, third and fourth strap guide members having a strap lock mounted thereon, wherein each strap lock is displaceable relative to said first, second, third and fourth strap guide members, respectively, between a locked and an unlocked position, said second longitudinal brace assembly has a first strap connection member, a second strap connection member, a third strap connection member and a fourth strap connection member mounted thereon, and each said first, second, third and fourth straps has a first end and a second end and is segmented into a first side segment on a first side of said orthopedic brace, a second side segment on a second side of said orthopedic brace, and a second end segment;

slidably engaging said first side segment of each said first, second, third and fourth straps with each said first, second, third and fourth strap guide members, respectively, mounted on said first longitudinal brace assembly and fixably attaching each said first side segments to each said first, second, third and fourth strap connection members, respectively, mounted on said second longitudinal brace assembly to set an arbitrary length of each said first side segments and to connect said first and second longitudinal brace assemblies to one another by means of said first side segments;

slidably engaging said second side segment of each said first, second, third and fourth straps with each said first, second, third and fourth strap guide members, respectively, and attaching each said second side segments to each said first, second, third and fourth strap attachment members to set an arbitrary length of each said second side segments, while maintaining each said second side segments disconnected from each said first, second, third and fourth strap connection members, respectively;

maintaining said strap lock of each said first, second, third and fourth strap guide members in said unlocked position so that each said strap locks is disengaged from each said first, second, third and fourth straps, respectively;

positioning a body section between said first and second longitudinal brace assemblies;

coupling each said first, second, third and fourth strap attachment members with each said first, second, third and fourth strap connection members, respectively, so that said second side segments connect said first and second longitudinal brace assemblies to one another about said body section;

displacing said second side segments to slide each said first, second, third and fourth straps through each said first, second, third and fourth strap guide members, respectively, to render said first side segments more taut;

displacing each strap lock from said unlocked position to said locked position, thereby changing each said first side segments from said arbitrary length to a desired fixed length; and displacing said second end segments to slide each said first, second, third and fourth straps through each said first, second, third and fourth strap attachment members, respectively, to render said second side segments more taut and change said second side segments from said arbitrary length to a desired fixed length.

2. The method of claim 1, wherein said body section is a leg having a lateral side and a medial side and having an upper leg, a lower leg and a knee joint, further wherein said orthopedic brace is a knee brace, said first longitudinal brace assembly is a lateral longitudinal brace assembly including a lateral upper support arm positioned adjacent said upper leg on said lateral side, a lateral central joint positioned adjacent said knee joint, and a lateral lower support arm positioned adjacent said lower leg on said lateral side and said second longitudinal brace assembly is a medial longitudinal brace assembly including a medial upper support arm positioned adjacent said upper leg on said medial side, a medial central joint positioned adjacent said knee joint on said medial side, and a medial lower support arm positioned adjacent said lower leg on said medial side after positioning said body section between said lateral and medial longitudinal brace assemblies.

3. The method of claim 2, wherein said first side segment is a posterior segment and said second side segment is an anterior segment.

4. The method of claim 2, wherein said first strap is an upper distal strap, said second strap is an upper proximal strap, said third strap is a lower proximal strap, said fourth strap is a lower distal strap, said first strap attachment member is an upper distal strap attachment member, said second strap attachment member is an upper proximal strap attachment member, said third strap attachment member is a lower proximal strap attachment member, said fourth strap attachment member is a lower distal strap attachment member, said first strap guide member is an upper distal strap guide member, said second strap guide member is an upper proximal strap guide member, said third strap guide member is a lower proximal strap guide member, said fourth strap guide member is a lower distal strap guide member, said first strap connection member is an upper distal strap connection member, said second strap connection member is an upper proximal strap connection member, said third strap connection member is a lower proximal strap connection member and said fourth strap connection member is a lower distal strap connection member.

5. The method of claim 1, further comprising uncoupling each said first, second, third and fourth strap attachment members from each said first, second, third and fourth strap connection members, respectively, so that said first and second longitudinal brace assemblies are disconnected from one another on said second side of said orthopedic brace and removing said first and second longitudinal brace assemblies from about said body section while maintaining said first side segments and said second side segments at said desired fixed lengths.

6. The method of claim 5, further comprising repositioning said body section between said first and second longitudinal brace assemblies and recoupling each said first, second, third and fourth strap attachment members with each said first, second, third and fourth strap connection members, respectively, so that said second side segments connect said first and second longitudinal brace assemblies to one another, while maintaining said first side segments and said second side segments at said desired fixed lengths during said repositioning and recoupling steps.

7. The method of claim 1, wherein said first and second longitudinal brace assemblies each has a first support arm, a second support arm, a central joint rotatably joining said first and second support arms, a first housing telescopingly displaceable relative to said central joint along said first support arm and a second housing telescopingly displaceable relative to said central joint along said second support arm, said method further comprising displacing said first housing relative to said central joint and/or displacing said second housing relative to said central joint after positioning said body section between said first and second longitudinal brace assemblies.

8. The method of claim 1, wherein said first and second longitudinal brace assemblies each has a first support arm, a second support arm, a central joint rotatably joining said first and second support arms, a first housing telescopingly displaceable relative to said central joint along said first support arm and a second housing telescopingly displaceable relative to said central joint along said second support arm, said method further comprising displacing said first housing relative to said central joint and/or displacing said second housing relative to said central joint after coupling said second and third strap attachment members with said second and third strap connection members, respectively, but before coupling said first and fourth strap attachment members with said first and fourth strap connection members, respectively.

9. The method of claim 1, further comprising transitioning said strap locks from said closed position to said open position, readjusting said positioning of said body section relative to said first longitudinal brace assembly or said second longitudinal brace assembly, and transitioning said strap locks from said open position to said closed position.

10. A method for fitting an orthopedic brace to a body section of a user comprising the steps of:
providing an orthopedic brace including a first longitudinal brace assembly, a second longitudinal brace assembly, a first strap, and a second strap, wherein said first and second straps each has a first end and a second end and is segmented between said first and second ends into a first side segment on a first side of said orthopedic brace and a second side segment on a second side of said orthopedic brace, said first and second side segments joined at a segment intersection;
attaching said first ends to said first longitudinal brace assembly and slidably connecting said segment intersections to said second longitudinal brace assembly such that said first side segments have an arbitrary length and connect said first and second longitudinal brace assemblies to one another on said first side of said orthopedic brace;
positioning a body section between said first and second longitudinal brace assemblies;
releasably fixably connecting said first and second straps to said first longitudinal brace assembly, thereby connecting said first and second longitudinal brace assemblies to one another about said body section on said second side of said orthopedic brace with said second side segments such that said second side segments have an arbitrary length;
adjusting said arbitrary length of said first side segments to a desired fixed length by sliding said first and second straps relative to said second longitudinal brace assembly, thereby varying a location of said segment intersection on said first and second straps;
releasably locking connection of said segment intersections to said second longitudinal brace assembly to substantially prevent sliding of said segment intersections relative to said second longitudinal brace assembly, thereby fixing said first side segments to said desired fixed length;
adjusting said arbitrary length of said second side segments to a desired fixed length without changing said desired fixed length of said first side segments or changing said location of said segment intersection on said first and second straps; and
fixing said second side segments to said desired fixed length.

11. The method of claim 10, wherein said body section is a leg having a lateral side and a medial side and having an upper leg, a lower leg and a knee joint, further wherein said orthopedic brace is a knee brace, said first longitudinal brace assembly is a lateral longitudinal brace assembly including a lateral upper support arm positioned adjacent said upper leg on said lateral side, a lateral central joint positioned adjacent said knee joint, and a lateral lower support arm positioned adjacent said lower leg on said lateral side and said second longitudinal brace assembly is a medial longitudinal brace assembly including a medial upper support arm positioned adjacent said upper leg on said medial side, a medial central joint positioned adjacent said knee joint on said medial side, and a medial lower support arm positioned adjacent said lower leg on said medial side after positioning said body section between said lateral and medial longitudinal brace assemblies.

12. The method of claim 11, wherein said first side segment is a posterior segment and said second side segment is an anterior segment.

13. The method of claim 11, wherein said first strap is an upper strap connecting said lateral and medial longitudinal brace assemblies to one another above said knee joint and said second strap is a lower strap connecting said lateral and medial longitudinal brace assemblies to one another below said knee joint.

14. The method of claim 10, wherein said first and second longitudinal brace assemblies each has a first support arm, a second support arm, and a central joint rotatably joining said first and second support arms, a first housing telescopingly displaceable relative to said central joint along said first support arm and a second housing telescopingly displaceable relative to said central joint along said second support arm, said method further comprising displacing said first housing relative to said central joint and/or displacing said second housing relative to said central joint after positioning said body section between said first and second longitudinal brace assemblies.

15. A method for fitting a knee brace to a leg of a user comprising the steps of:
providing a knee brace including a first essentially rigid support member, a second essentially rigid support member, and a strap, wherein said strap has a first end and a second end and is segmented between said first and second ends into a first side segment on a first side of said knee brace and a second side segment on a second side of said knee brace, said first and second side segments joined at a segment intersection and in total defining an encircling segment;

positioning said first support member on a first side of a leg above or below a knee joint;

positioning said second support member on a second side of said leg above or below said knee joint;

attaching said first end to said first support member and slidably connecting said segment intersection to said second support member such that said first side segment has an arbitrary length and connects said first and second support members to one another on said first side of said knee brace;

positioning a body section between said first and second support members;

releasably fixably connecting said strap to said first support member, thereby connecting said first and second support members to one another about said body section on said second side of said knee brace with said second side segment such that said second side segment has an arbitrary length;

adjusting said arbitrary length of said first side segment to a desired fixed length by sliding said strap relative to said second support member, thereby varying a location of said segment intersection on said strap;

releasably locking connection of said segment intersection to said second support member to substantially prevent sliding of said segment intersection relative to said second support member, thereby fixing said first side segment to said desired fixed length corresponding to one or more dimensions of said body section;

adjusting said arbitrary length of said second side segment to a desired fixed length without changing said desired fixed length of said first side segments or changing said location of said segment intersection on said strap; and fixing said second side segment to said desired fixed length.

16. The method of claim 15, wherein said support member is a first support arm attached to a first rotatable hinge and said second support member is a second support arm attached to a second rotatable hinge.

17. The method of claim 15, wherein said first side of said leg is a lateral side and said second side of said leg is a medial side.

18. The method of claim 10 further comprising:

releasing fixable connection of said first and second straps to said first longitudinal brace assembly;

unlocking slidable connection of said segment intersections to said second longitudinal brace assembly;

repositioning said first longitudinal brace assembly or said second longitudinal brace assembly relative to said body section;

relocking slidable connection of said segment intersections to said second longitudinal brace assembly; and fixably reconnecting said first and second straps to said first longitudinal brace assembly.

19. The method of claim 15 further comprising:

disconnecting said strap from said first support member;

repositioning said first support member or said second member relative to said leg, while maintaining said encircling segment at said desired fixed length; and fixably reconnecting said strap to said first support member.

* * * * *